United States Patent
Kahvejian et al.

(10) Patent No.: US 12,282,499 B1
(45) Date of Patent: Apr. 22, 2025

(54) DATABASE PROCESSING SYSTEM FOR DETERMINING WHETHER AN ENTITY AFFECTS A TRANSITION

(71) Applicant: Flagship Pioneering Innovations VI, LLC, Cambridge, MA (US)

(72) Inventors: Avak Kahvejian, Lexington, MA (US); Nicholas McCartney Plugis, Boston, MA (US); Michael Raymond Retchin, Columbus, OH (US); Fabian Alexander Wolf, Munich (DE); Poorya Hosseini, Cambridge, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 18/485,119

(22) Filed: Oct. 11, 2023

Related U.S. Application Data

(63) Continuation of application No. 16/511,691, filed on Jul. 15, 2019.

(60) Provisional application No. 62/805,888, filed on Feb. 14, 2019, provisional application No. 62/805,884, filed on Feb. 14, 2019, provisional application No. 62/698,701, filed on Jul. 16, 2018.

(51) Int. Cl.
*G06F 16/28* (2019.01)
*G16B 50/00* (2019.01)

(52) U.S. Cl.
CPC .......... *G06F 16/288* (2019.01); *G16B 50/00* (2019.02)

(58) Field of Classification Search
CPC .................................................... G16B 50/00
See application file for complete search history.

(56) References Cited

U.S. PATENT DOCUMENTS

| | | |
|---|---|---|
| 2004/0259073 A1 | 12/2004 | Hassibi et al. |
| 2007/0238094 A1 | 10/2007 | Chaussabel et al. |
| 2008/0033658 A1 | 2/2008 | Dalton et al. |
| 2008/0294403 A1 | 11/2008 | Zhu et al. |
| 2010/0036192 A1 | 2/2010 | Yao et al. |
| 2010/0255471 A1 | 10/2010 | Clarke et al. |
| 2013/0116130 A1 | 5/2013 | Fu et al. |
| 2014/0030255 A1 | 1/2014 | Loboda et al. |
| 2014/0206546 A1 | 7/2014 | Chenchik |
| 2014/0228236 A1 | 8/2014 | Anastassiou |
| 2014/0236495 A1 | 8/2014 | Thiery et al. |
| 2015/0154352 A1 | 6/2015 | Johnson et al. |
| 2016/0245796 A1 | 8/2016 | Weinberger et al. |
| 2016/0253453 A1 | 9/2016 | Janes et al. |
| 2016/0289670 A1 | 10/2016 | Samuels et al. |
| 2016/0303133 A1 | 10/2016 | Dudley et al. |
| 2016/0312302 A1 | 10/2016 | Clarke et al. |
| 2016/0326593 A1 | 11/2016 | Clement et al. |
| 2017/0057890 A1 | 3/2017 | Kawai et al. |
| 2017/0076035 A1 | 3/2017 | Califano et al. |
| 2017/0154163 A1 | 6/2017 | Arnon et al. |
| 2017/0260584 A1 | 9/2017 | Zheng et al. |
| 2017/0262576 A1 | 9/2017 | Buzdin et al. |
| 2017/0270241 A1 | 9/2017 | Garry et al. |
| 2017/0275669 A1* | 9/2017 | Weissleder ........... C12Q 1/6816 |
| 2017/0344866 A1 | 11/2017 | Fan et al. |
| 2017/0362654 A1 | 12/2017 | Murphy |
| 2018/0030515 A1 | 2/2018 | Regev et al. |
| 2018/0088112 A1 | 3/2018 | Fan et al. |
| 2018/0100201 A1 | 4/2018 | Garraway et al. |
| 2018/0127823 A1 | 5/2018 | Shekhar et al. |
| 2018/0165414 A1 | 6/2018 | Almarode et al. |
| 2018/0216197 A1 | 8/2018 | Davicioni et al. |
| 2018/0225416 A1 | 8/2018 | Wong et al. |
| 2018/0340890 A1 | 11/2018 | Roederer et al. |
| 2018/0341744 A1 | 11/2018 | Regev et al. |
| 2018/0355407 A1 | 12/2018 | Utharala et al. |
| 2018/0365372 A1 | 12/2018 | Araya et al. |
| 2018/0371545 A1 | 12/2018 | Wong et al. |

(Continued)

FOREIGN PATENT DOCUMENTS

| | | |
|---|---|---|
| CN | 106777870 | 5/2017 |
| CN | 107451424 | 12/2017 |

(Continued)

OTHER PUBLICATIONS

Aran, et al., "Reference-based analysis of lung single-cell sequencing reveals a transitional profibrotic macrophage," Nature Immunology, vol. 20, No. 2, Feb. 2019, pp. 163-172.

Brennecke, et al.,"Accounting for technical noise in single-cell RNA-seq experiments," Nature Methods, vol. 10, No. 11, Nov. 2013, 7 pages.

Chen, et al., "DensityPath: an algorithm to visualize and reconstruct cell state-transition path on density landscape for single-cell RNA sequencing data," Bioinformatics (Oxford, England), Dec. 7, 2018.

Clark, et al., "The characteristic direction: a geometrical approach to identify differentially expressed genes," BMC Bioinformatics 2014, 15:79, 15 pages.

Dixit, et al., "Perturb-Seq: Dissecting Molecular Circuits with Scalable Single-Cell RNA Profiling of Pooled Genetic Screens," Cell, vol. 167, No. 7, Dec. 15, 2016, pp. 1853-1866.

(Continued)

*Primary Examiner* — Jerry Lin

(57) ABSTRACT

A database processing system performs a first database access call accessing a first construct representing a differential component amount between a normal and different state. This identifies a plurality of components and, for each, a corresponding first association between (a) a change in amount of the respective component in a first plurality of first component datasets and a second plurality of second component datasets and (b) a change in state between the normal and different state. A second database access call accesses a second construct representing a measure of differential component amount between a native and exposed sample. The second construct identifies all or a portion of the plurality of components and, for each, a corresponding second association between a change of amount of the respective component between a third and fourth plurality of component datasets. The first associations and corresponding second associations determine whether the entity affects the transition.

15 Claims, 10 Drawing Sheets

(56) References Cited

U.S. PATENT DOCUMENTS

| | | | |
|---|---|---|---|
| 2018/0372726 | A1 | 12/2018 | Lo et al. |
| 2019/0005304 | A1 | 1/2019 | Adalsteinsson et al. |
| 2019/0071718 | A1 | 3/2019 | Santhanam et al. |
| 2019/0078149 | A1 | 3/2019 | Sawa et al. |
| 2019/0085324 | A1 | 3/2019 | Regev et al. |
| 2019/0085396 | A1 | 3/2019 | Apte et al. |
| 2019/0093154 | A1 | 3/2019 | Shalek et al. |
| 2019/0094223 | A1 | 3/2019 | Shen-Orr et al. |
| 2019/0142722 | A1 | 5/2019 | Christiano |
| 2019/0204299 | A1 | 7/2019 | Mead et al. |

FOREIGN PATENT DOCUMENTS

| | | |
|---|---|---|
| CN | 109033743 | 12/2018 |
| CN | 109486750 | 3/2019 |
| CN | 109628555 | 4/2019 |
| WO | WO2002037102 A2 | 5/2002 |
| WO | WO 2014165823 A1 | 10/2014 |
| WO | WO 2016191533 A1 | 12/2016 |
| WO | WO 2017/075294 A1 | 5/2017 |
| WO | WO 2017083817 A1 | 5/2017 |
| WO | WO 2018005691 A1 | 1/2018 |
| WO | WO 2018058249 A1 | 4/2018 |
| WO | WO 2018132635 A1 | 7/2018 |
| WO | WO 2018140302 A1 | 8/2018 |
| WO | WO 2018154027 A1 | 8/2018 |
| WO | WO 2018183908 A1 | 10/2018 |
| WO | WO 2018191553 A1 | 10/2018 |
| WO | WO 2018204854 A1 | 11/2018 |
| WO | WO 2018209324 A2 | 11/2018 |
| WO | WO 2018232195 A1 | 12/2018 |
| WO | WO 2019010486 A1 | 1/2019 |
| WO | WO 2019014581 A1 | 1/2019 |
| WO | WO 2019018441 A1 | 1/2019 |
| WO | WO 2019018684 A1 | 1/2019 |
| WO | WO 2019079362 A1 | 4/2019 |
| WO | WO 2019084046 A1 | 5/2019 |

OTHER PUBLICATIONS

Dudley, et al., "Computational Repositioning of the Anticonvulsant Topiramate for Inflammatory Bowel Disease," Science Transitional Medicine, vol. 3, Issue 96, Aug. 17, 2017, 8 pages.

Gong, et al., "Molecular Signature of Early Cardiovascular Lineages Revealed by Single Cell Transcriptomics," Circulation, vol. 132, No. Suppl. 3, Nov. 10, 2015, pp. 18849.

Hodos, et al., "Computational Approaches to Drug Repurposing and Pharmacology," Wiley interdiscip Rev Syst Biol Med. 8(3), May 2016, pp. 186-210.

Jang, et al., "Dynamics of embryonic stem cell differentiation inferred from single-cell transcriptomics show a series of transitions through discrete cell states," eLife, vol. 6, Mar. 15, 2017, pp. Article No. e20487.

Jin, et al., "scEpath: energy landscape-based inference of transition probabilities and cellular trajectoris from single-cell transcriptomic data," Bioinformatics, 34(12), 2018, pp. 2077-2086.

Kemmeren, et al., "Large-Scale Genetic Perturbations Reveal Regulatory Networks and an abundance of Gene-Specific Repressors," Cell, vol. 157, No. 3, Apr. 24, 2014, pp. 740-752.

Levitin, et al., "De novo gene signature identification from single-cell RNA-seq with hierarchical Poisson factorization," Molecular Systems Biology, vol. 15, No. 2, Feb. 2019, pp. Article No. e8557.

Lu, et al., "Molecular Signature of Megakaryocyte-Erythroid Progenitors Reveals Role of Cell Cycle in Fate Specification," Blood, vol. 132, No. Suppl. 1, Nov. 29, 2018, pp. 3828.

Macosko, et al., "Highly Parallel Genome-wide Expression Profiling of Individual Cells Using Nanoliter Droplets," Cell 161, May 21, 2015, pp. 1202-1214.

Mukherjee, et al., "Identifying progressive gene network perturbation from single-cell RNA-seq data," IEEE Engineering in Medicine and Biology Society. Annual Conference, vol. 2018, Jul. 2018, pp. 5034-5040.

Nguyen, et al., "Single-cell RNA-seq of human induced pluripotent stem cells reveals cellular heterogeneity and cell state transitions between subpopulations," Genome Research, vol. 27, No. 7, Jul. 2018, pp. 1053-1066.

Olsson, et al., "Single-cell analysis of mixed-lineage states leading to a binary cell fate choice," Nature, vol. 537, Sep. 29, 2019, 23 pages.

O'Sullivan, et al., "Reconstruction of Transcriptional Programs of Monocyte to Macrophage Sequential Cell Fate Transition Using Single Cell RNA Sequencing in Sex Mis-Matched Lung Transplantation," The Journal of Heart and Lung Transplantation, vol. 38, No. 4, Apr. 2019, pp. S157.

Reid, et al., "Transdifferentiation: do transition states lie on the path of development?" Current Opinion in systems biology, vol. 11, Oct. 2018, pp. 18-23.

Teschendorff, et al., "Denoising perturbation signatures reveal an actionable AKT-signaling gene module underlying a poor clinical outcome in endocrine-treated ER+ breast cancer," Genome Biology, vol. 16, Apr. 2, 2015, pp. 61.

Wolf, et al., "SCANPY: large-scale single-cell gene expression data analysis," Genome Biology, 2018, pp. 1-5.

Wolf, et al., "PAGA: graph abstraction reconciles clustering with trajectorty inference through a topology preserving map of single cells," Genome Biology, 2019, pp. 1-9.

Xie, et al., "Experimental and Computational Approaches for Single-Cell Enhancer Perturbation Assay," Methods in molecular biology (Clifton, NJ), 2019, vol. 1935, pp. 203-221.

Xu, et al., "Accurate Drug Repositioning through Non-tissue-Specific Core Signatures from Cancer Transcriptomes," Cell Reports, vol. 25, No. 2, Oct. 9, 2018, pp. 523-535.

Bargaje, et al., "Cell population structure prior to bifurcation predicts efficiency of directed differentiation in human induced pluripotent cells," PNAS, vol. 14, No. 9, Feb. 28, 2017, pp. 2271-2276.

Carro, et al., "The transcriptional network for mesenchymal transformation of brain tumors," Nature, vol. 463, Jan. 21, 2010, 24 pages.

George, et al., "Survival Outcomes in Cancer Patients Predicted by a Partial EMT Gene Expression Scoring Metric," Cancer Research, vol. 77, No. 22, Sep. 25, 2017, pp. 6415-6428.

International Search Report & Written Opinion, PCT Application No. PCT/ US19/41976, dated Oct. 15, 2019, 13 pages.

Jerby-Arnon, et al., "A Cancer Cell Program Promotes T Cell Exclusion and Resistance To Checkpoint Blockade," Cell 175, Nov. 1, 2018, pp. 984-997.

Kahvejian, et al., "What would you do if you could sequence everything?" Nat Biotechnol. vol. 26, No. 10, Oct. 2008, 23 pages.

Lamb, et al., "The Connectivity Map: Using Gene-Expression Signatures to Connect Small Molecules, Genes, and Disease," Science, vol. 313, Sep. 29, 2006, pp. 1929-1935.

Mead, et al., "Harnessing single-cell genomics to improve the physiological fidelity of organoid-derived cell types," BMC Biology, 16:62, 2018, 24 pages.

Welch, et al., "Matcher: manifold alignment reveals correspondence between single cell transcriptome and epigenome dynamics," Genome Biology, vol. 18, Jul. 24, 2017, pp. 1-19.

Fard, et al., "Modeling the Attractor Landscape of Disease Progression: a Network-Based Approach," Frontiers in Genetics, vol. 8, 12 pages, Apr. 18, 2017.

Jindal et al., A Review on Dimensionality Reduction Techniques., International Journal of Computer Applications (0975-8887) vol. 173—No. 2, Sep. 2017.

Mair et al. "Gain-and loss-of-function mutations in the breast cancer gene GATA3 result in differential drug sensitivity." PLoS genetics 12.9 (2016): e1006279. (Year: 2016).

Moon, et al. Manifold learning-based methods for analyzing single-cell RNA-sequencing data. Current Opinion in Systems Biology 2018, 7:36-46 (Year: 2018).

\* cited by examiner

200

*(202)* Access, in electronic form, a single-cell transition signature representing a measure of differential cellular-component expression between a first cell state and an altered cell state. The altered cell state occurs through the cellular transition from the first cell state to the altered cell state. The single-cell transition signature includes an identification of a plurality of cellular-components. For each respective cellular-component in the plurality of cellular-components, a corresponding first significance score quantifies an association between a change in expression of the respective cellular-component and a change in cell state between the first cell state and the altered cell state.

*(204)* Access, in electronic form, a perturbation signature representing a measure of differential cellular-component expression between a plurality of unperturbed cells and a plurality of perturbed cells exposed to the perturbation. The perturbation signature includes an identification of all or a portion of the plurality of cellular-components and, for each respective cellular-component in the all or the portion of the plurality of cellular-components, a corresponding second significance score that quantifies an associated between a change in expression of the respective cellular-component between the plurality of unperturbed cells and the plurality of perturbed cells and a change in cell state between the plurality of unperturbed cells and the plurality of perturbed cells.

*(206)* Compare the single-cell transition signature and the perturbation signature to determine whether the perturbation will affect the cellular transition.

Figure 2

Single cell RNA-sequencing measurements

Force-Directed Layout Algorithm

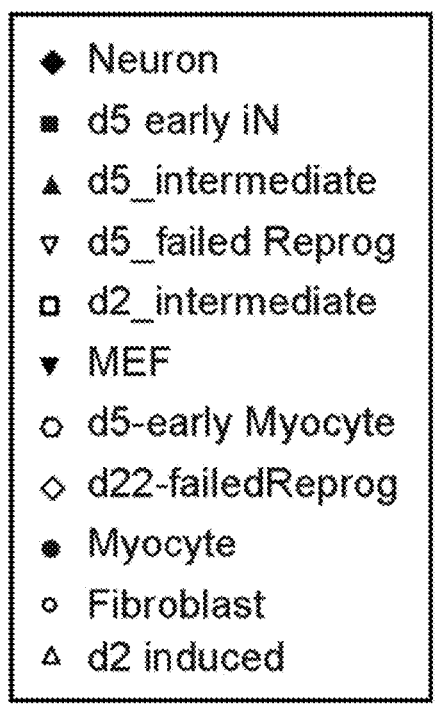
Figure 5A
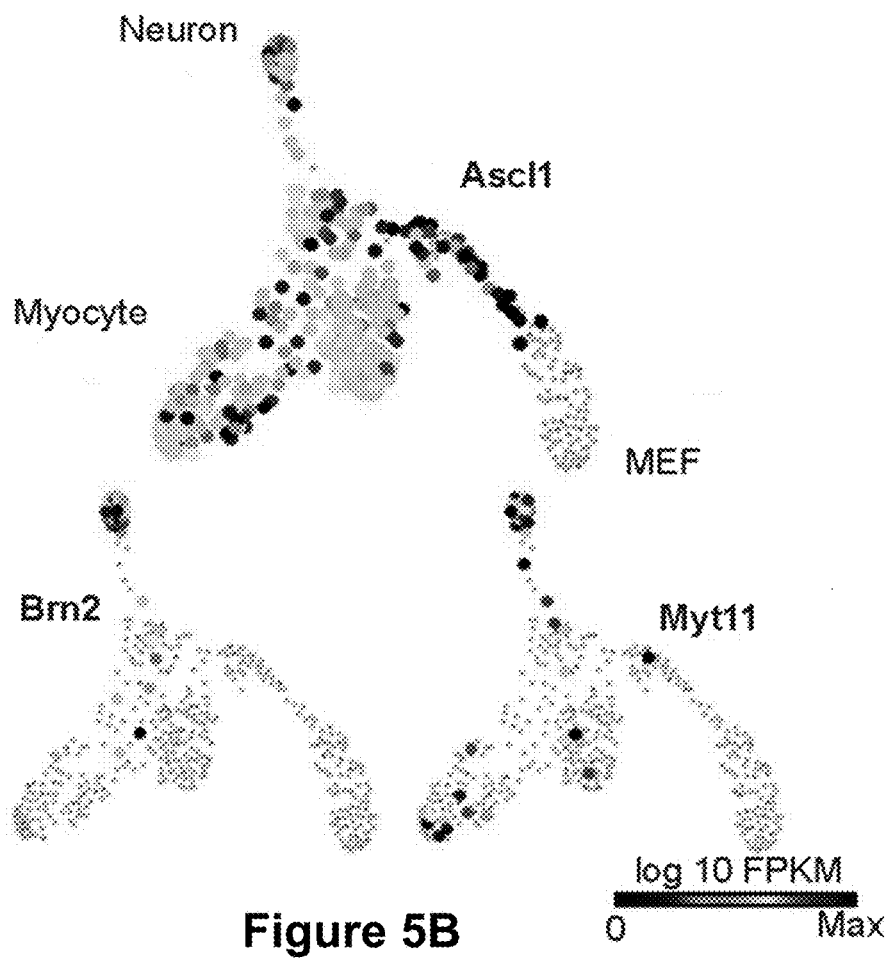
Figure 5B

DATABASE PROCESSING SYSTEM FOR DETERMINING WHETHER AN ENTITY AFFECTS A TRANSITION

PRIORITY CLAIM

This application is a continuation of U.S. application Ser. No. 16/511,691, filed Jul. 15, 2019, which claims priority under 35 U.S.C. §§ 119(e) to U.S. Provisional Application No. 62/805,888, filed Feb. 14, 2019, U.S. Provisional Application No. 62/805,884, filed Feb. 14, 2019 and U.S. Provisional Application No. 62/698,701, filed Jul. 16, 2018.

TECHNICAL FIELD

The present invention relates generally to methods for analyzing whether an entity affects a transition.

BACKGROUND

What is needed in the art are systems and methods that enable enhanced cell analysis. In particular, there is a need for enabling a prediction whether a perturbation will affect a cell transition.

SUMMARY

The present disclosure addresses the above-identified shortcomings. The present disclosure addresses these shortcomings, at least in part, with single cell data and perturbation data as key data substrates, and using machine learning to refine understanding of natural diverse states, revealing key transition states, driving understanding of the mechanisms underlying state changes, and discovering approaches for controlling these state changes.

Yet another aspect of the present disclosure provides a non-transitory computer readable storage medium, where the non-transitory computer readable storage medium stores instructions, which when executed by a computer system, cause the computer system to perform any of the methods for analyzing cells described in the present disclosure.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIG. 2 provides a flow chart of processes and features of a system for analyzing cells, in accordance with various embodiments of the present disclosure, wherein elements in dashed boxes are optional;

FIG. 5A depicts the manifold of FIG. 5B, in accordance with an embodiment of the present disclosure;

FIG. 5B depicts the level of expression of each of the BAM transcription factors in each of the cells on each of the measurement days depicted as points in the manifold of FIG. 4B, in accordance with an embodiment of the present disclosure;

DETAILED DESCRIPTION

Figure 1:
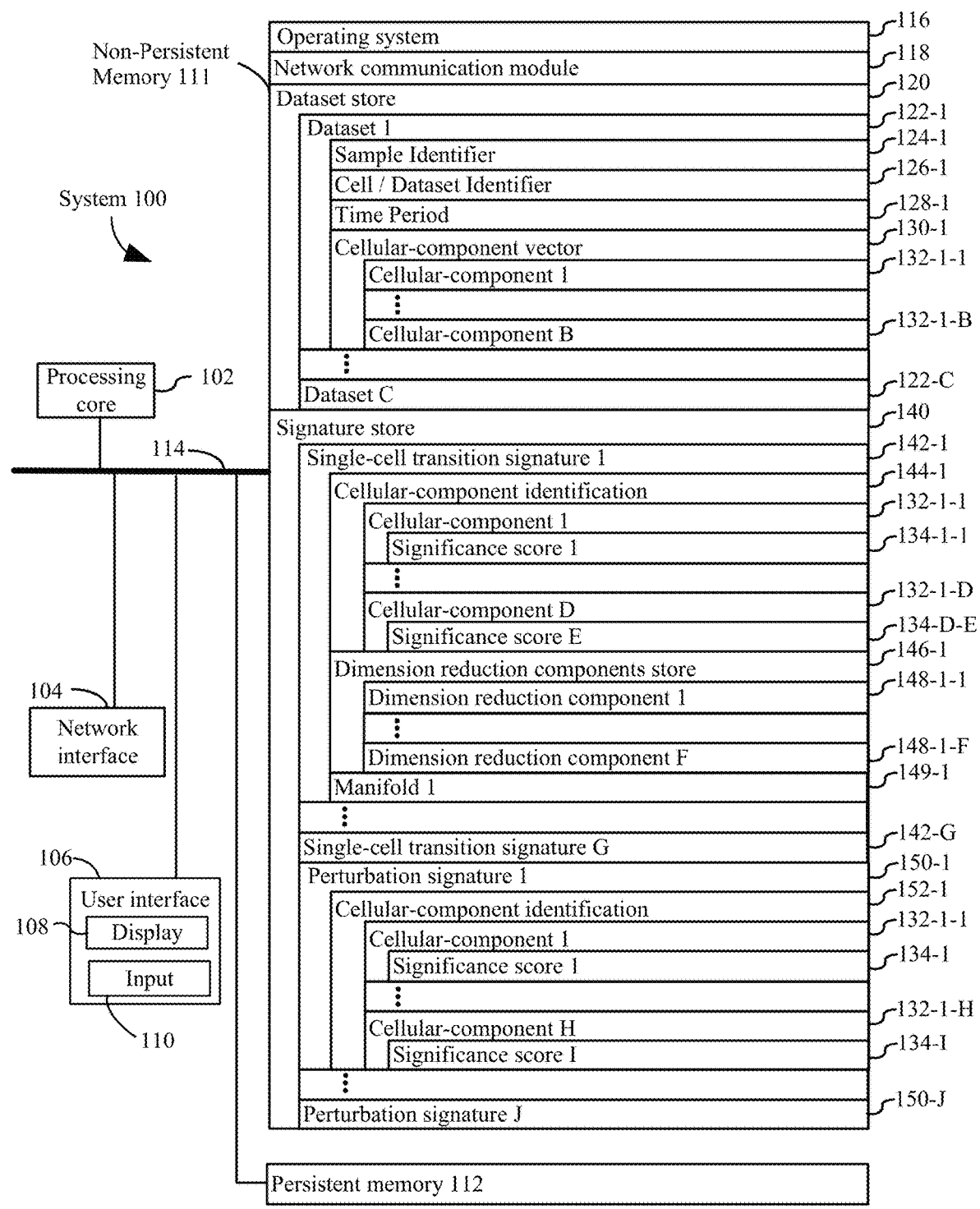
FIG. 1 illustrates a block diagram of an exemplary system and computing device, in accordance with an embodiment of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Plural instances may be provided for components, operations or structures described herein as a single instance. Finally, boundaries between various components, operations, and data stores are somewhat arbitrary, and particular operations are illustrated in the context of specific illustrative configurations. Other forms of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first dataset could be termed a second dataset, and, similarly, a second dataset could be termed a first dataset, without departing from the scope of the present invention. The first dataset and the second dataset are both datasets, but they are not the same dataset.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

Furthermore, when a reference number is given an "$i^{th}$" denotation, the reference number refers to a generic component, set, or embodiment. For instance, a cellular-component termed "cellular-component i" refers to the $i^{th}$ cellular-component in a plurality of cellular-components.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

As used herein, the term "perturbation" in reference to a cell (e.g., a perturbation of a cell or a cellular perturbation) refers to any treatment of the cell with one or more compounds. These compounds can be referred to as "perturbagens." In some embodiments, the perturbagen can include, e.g., a small molecule, a biologic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other gene editing system), or any combination of any of the foregoing.

As used herein, the term "progenitor" in reference to a cell (e.g., a progenitor cell) refers to any cell that is capable of transitioning from one cell state to at least one other cell state.

As used herein, the term "dataset" in reference to cellular-component expression measurements for a cell or a plurality of cells can refer to a high-dimensional set of data collected from a single cell (e.g., a single-cell cellular-component expression dataset) in some contexts. In other contexts, the term "dataset" can refer to a plurality of high-dimensional sets of data collected from single cells (e.g., a plurality of single-cell cellular-component expression datasets), each set of data of the plurality collected from one cell of a plurality of cells.

As used herein, the term "affect" refers to change in a cellular transition.

L. Exemplary System Embodiments

Now that an overview of some aspects of the present disclosure and some definitions used in the present disclosure have been provided, details of an exemplary system are described in conjunction with FIG. 1.

FIG. 1 provides a block diagram illustrating a system 100 in accordance with some embodiments of the present disclosure. The system 100 provides a prediction if a perturbation will affect a cell transition. In FIG. 1, the system 100 is illustrated as a computing device. Of course, other topologies of the computer system 100 are possible. For instance, in some embodiments, the system 100 can in fact constitute several computer systems that are linked together in a network, or be a virtual machine or a container in a cloud computing environment. As such, the exemplary topology shown in FIG. 1 merely serves to describe the features of an embodiment of the present disclosure in a manner that will be readily understood to one of skill in the art.

Referring to FIG. 1, in some embodiments a computer system 100 (e.g., a computing device) includes a network interface 104. In some embodiments, the network interface 104 interconnects the system 100 computing devices within the system with each other, as well as optional external systems and devices, through one or more communication networks (e.g., through network communication module 118). In some embodiments, the network interface 104 optionally provides communication through network communication module 118 via the Internet, one or more local area networks (LANs), one or more wide area networks (WANs), other types of networks, or a combination of such networks.

Examples of networks include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11 n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

The system 100 in some embodiments includes one or more processing units (CPU(s)) 102 (e.g., a processor, a processing core, etc.), one or more network interfaces 104, a user interface 107 including (optionally) a display 108 and an input system 110 (e.g., an input/output interface, a keyboard, a mouse, etc.) for use by the user, memory (e.g., non-persistent memory 111, persistent memory 112), and one or more communication buses 114 for interconnecting the aforementioned components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, include non-transitory computer readable storage medium. In some embodiments, the non-persistent memory 111 or alternatively the non-transitory computer readable storage medium stores the following programs, modules and data structures, or a subset thereof, sometimes in conjunction with the persistent memory 112:

- an optional operating system 116 (e.g., ANDROID, iOS, DARWIN, RTXC, LINUX, UNIX, OS X, WINDOWS, or an embedded operating system such as VxWorks), which includes procedures for handling various basic system services and for performing hardware dependent tasks;
- an optional network communication module (or instructions) 118 for connecting the system 100 with other devices and/or a communication network 104;
- a dataset store 120 that stores a plurality of datasets 122, each dataset including one or more identifiers (e.g., sample identifier 124 and/or cell/dataset identifier 126), an associated period of time 128, and a cellular component vector 130 including one or more cellular components 132; and
- a signature store 140 that stores one or more single-cell transition signatures 142 and one or more perturbation signatures 150.

As described above, the dataset store 120 includes a plurality of datasets 120. Each dataset is obtained (e.g., collected, communicated, etc.) from a single-cell measurement (e.g., single-cell measurement 310 of FIG. 3) of a population of cells (e.g., a respective sample). The sample identifier (ID) 124 associated with each dataset 122 indicates which sample a cell's dataset came from. The cell/dataset identifier 126 indicates which cell and/or plurality of datasets (e.g., subset of datasets) the dataset 122 is associated with and/or a state of the cell. In some embodiments, the time period 128 is associated with a period of time of capture of the dataset 122 (e.g., when during the growth of the cell such as a first time period to when the cell is initially cultured, a second time period $t_1$ when measurement of cellular expression occurs, etc.).

Furthermore, in some embodiments each dataset 120 includes a cellular-component vector 130 including one or more cellular-components 132. In some embodiments, the one or more cellular-components 132 includes all cellular-components of the cell or a subset of these the cellular-components of the cell. Each cellular-component 132 represents a dimension of data related to a measurement (e.g., single-cell measurement 310 of FIG. 3). Generally, the datasets 122 include a high (e.g., greater than 3, greater than 5, greater 10, greater than 100, etc.) dimensionality, which includes a large amount of data. Moreover, in some embodiments each dataset 122 is obtained from a cell in a plurality of cells (e.g., from a sample) that have transitioned away from a "progenitor" cell type (e.g., from a first state to an altered state).

In some embodiments, the system includes the signature store 140 that stores one or more single-cell transition signatures 142 and one or more perturbation signature 150. In some embodiments, the one or more single-cell transition signatures 142 include one or more predetermined signatures (e.g., a training signature). In some embodiments, the one or more single-cell transition signatures 142 include a single-cell transition signature that is determined by the system 100, and/or stored within the system for future use. Each single-cell transition signatures 142 includes a cellular-component identification 144 that further includes a plurality of cellular components (e.g., cellular-components 132-1-1 through 132-1-D of FIG. 1). Furthermore, each cellular component 132 associated with the single-cell transition signature 142 includes a corresponding significance score 134. In some embodiments, dimensionality reduction is performed (e.g., dimensionality reduction 320 of FIG. 3) on a dataset 122, which generates (e.g., stores within a dimension reduction components store 146-1 of FIG. 1 and/or generate Matrix M of FIG. 3) a plurality of dimension reduction components 148 (e.g., dimension reduction component 148-1-1 through dimension reduction component 148-1-F of FIG. 1). Accordingly, the system 100 in some embodiments performs a dimensionality reduction (e.g., dimensionality reduction 320 of FIG. 3) to generate a plurality of dimension reduction components 148 (e.g., generate Matrix M of FIG. 3), preserving latent patterns present in the cellular components 132 of the dataset 122. In some embodiments, the output of this dimensionality reduction (e.g., dimensionality reduction components reduction components 148-1-1 through 148-1-F of FIG. 1) is a matrix (e.g., Matrix M as referred to infra.), which encodes the dataset 122 in a compressed form while also maintaining the underlying latent structure of the dataset.

In some embodiments, the signature transition store includes a manifold 149. In some embodiments, this manifold 149 is associated with the corresponding dimension reduction components 148 of the single-cell transition signature 142. This manifold 149 is identified by performing a manifold learning with the cellular-component vectors 130 of the datasets 122 associated with the manifold (e.g., datasets 122 associated with the single-cell transition signature 142).

The signature store 140 further includes one or more perturbation signatures 150 associated with a corresponding perturbation. Each perturbation signature includes a cellular-component identification 152 that includes a plurality of cellular-components (e.g., cellular-component 132-1-1 through 132-1-H of FIG. 1). In some embodiments, the cellular-components of the cellular-components identification 152 includes some or all of the cellular-components associated with a corresponding single-cell transition signature 144 (e.g., cellular-components identification 152 of perturbation signature 150-1 includes a subset of cellular-components identification 144 of single-cell transition signature 142-1 of FIG. 1). Furthermore, each cellular component of the perturbation signature 150 includes a corresponding significance score 134.

In various embodiments, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of the system 100, that is addressable by the system 100 so that the system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules instead may be stored in persistent memory 112 or in more than one memory. For example, in some embodiments, at least dataset store 120 is stored in a remote storage device which can be a part of a cloud-based infrastructure. In some embodiments, at least dataset store 120 is stored on a cloud-based infrastructure. In some embodiments, dataset store 120 and signature store 140 can also be stored in the remote storage device(s).

While a system in accordance with the present disclosure has been disclosed with reference to FIG. 1, a method 200 in accordance with the present disclosure is now detailed with reference to FIG. 2.

Block 202. Referring to block 202 of FIG. 2, the method includes accessing (e.g., in electronic form) a single-cell transition signature (e.g., single-cell transition signature 142-1 of FIG. 1). The single-cell transition signature 142 represents a measure of differential cellular-component expression between a first cell state and an altered cell state. The altered cell state occurs through the cellular transition from the first cell state to the altered cell state. The single-cell transition signature 142 includes an identification (e.g., cellular-component identification 144-1 of FIG. 1) of a plurality of cellular-components. For each respective cellular-component in the plurality of cellular-components (e.g., cellular-component 132-1-1 through cellular-component 132-1-D of FIG. 1), a corresponding first significance score (e.g., signification score 134-1-1) quantifies an association between a change in expression of the respective cellular-component and a change in cell state between the first cell state and the altered cell state.

In some embodiments, accessing the single-cell transition signature includes determining the single-cell transition signature 142. This determining is based on a first plurality of first single-cell cellular-component expression datasets (e.g., dataset 122-1, dataset 122-2, and dataset 122-3), and a second plurality of second single-cell cellular-component expression datasets (e.g., dataset 122-4, dataset 122-5, and dataset 122-6). Each respective first single-cell cellular-component expression dataset 122 in the first plurality of first single-cell cellular-component expression datasets is obtained from a corresponding single cell of a first plurality of cells in the first cell state (e.g., single-cell measurement 310 of FIG. 3). Furthermore, each respective second single-cell cellular-component expression dataset in the second plurality of second single-cell cellularity component expression datasets is obtained from a corresponding single cell of a second plurality of cells in the altered cell state (e.g., single-cell measurement 310 of FIG. 3).

In some embodiments, determining the single-cell transition signature includes determining a difference in cellular-component quantities across the plurality of cellular-components 132. This difference is between the first plurality of first single-cell cellular-component expression datasets and the second plurality of second single-cell cellular-component expression datasets. In some embodiments, this difference is determined using one of a difference of means test, a Wilcoxon rank-sum test, a t-test, a logistic regression, or a generalized linear model.

In some embodiments, each respective dataset 122 of the first plurality of single-cell cellular-component expression datasets includes a corresponding cellular-component vector (e.g., cellular-component vector 130-1 of dataset 122-1 of FIG. 1), in a first plurality of cellular-component vectors. Furthermore, each respective dataset of the second plurality of single-cell cellular-component expression datasets includes a corresponding cellular-component vector in a second plurality of cellular-component vectors (e.g., cellular-component vector 130-2 of dataset 122-2). Each respective cellular-component vector in the first and second plurality of cellular-component vectors includes a plurality of elements. Each respective element in the respective cellular-component vector 130 is associated with a corresponding cellular-component 132 in the plurality of cellular-components and includes a corresponding value that represents a quantity of the corresponding cellular-component for the corresponding single cell that is represented by the respective dataset of the first and second pluralities of single-cell cellular-component expression datasets (e.g., cellular components and values of Table 2).

Furthermore, in some embodiments the cellular components 132 includes a plurality of genes. Additionally, in some embodiments one or more datasets 122 is generated using a method including single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combinations thereof (e.g., a method of Table 1).

Block 204. Referring to block 204, the method further includes accessing (e.g., in electronic form) a perturbation signature (e.g., perturbation signature 150-1 of FIG. 1). The perturbation signature 150 represents a measure of differential cellular-component expression between a plurality of unperturbed cells and a plurality of perturbed cells exposed to the perturbation. The perturbation signature 150 includes an identification (e.g., cellular-component identification 152-1 of FIG. 1) of all or a portion of the plurality of cellular-components. For each respective cellular-component in the all or the portion of the plurality of cellular-components (e.g., cellular-component 132-3-1 through cellular-component 132-3-D of FIG. 1), a corresponding second significance score (e.g., significance score 134 of FIG. 1) that quantifies an association between a change in expression of the respective cellular-component between the plurality of unperturbed cells and the plurality of perturbed cells and a change in cell state between the plurality of unperturbed cells and the plurality of perturbed cells.

In some embodiments, the method 200 includes performing dimensionality reduction (e.g., dimensionality reduction 320 of FIG. 3) on the first and/or the second plurality of single-cell cellular-component expression datasets 122. This dimensionality reduction generates a plurality of dimension reduction components (e.g., dimension reduction components 148 of FIG. 1). In some embodiments, the dimension reduction is a principal components algorithm, a random projection algorithm, an independent component analysis algorithm, or a feature selection method. a factor analysis algorithm, Sammon mapping, curvilinear components analysis, a stochastic neighbor embedding (SNE) algorithm, an Isomap algorithm, a maximum variance unfolding algorithm, a locally linear embedding algorithm, a t-SNE algorithm, a non-negative matrix factorization algorithm, a kernel principal component analysis algorithm, a graph-based kernel principal component analysis algorithm, a linear discriminant analysis algorithm, a generalized discriminant analysis algorithm, a uniform manifold approximation and projection (UMAP) algorithm, a LargeVis algorithm, a Laplacian Eigenmap algorithm, or a Fisher's linear discriminant analysis algorithm. See, for example, Fodor, 2002, "A survey of dimension reduction techniques," Center for Applied Scientific Computing, Lawrence Livermore National, Technical Report UCRL-ID-148494; Cunningham, 2007, "Dimension Reduction," University College Dublin, Technical Report UCD-CSI-2007-7, Zahorian et al., 2011, "Nonlinear Dimensionality Reduction Methods for Use with Automatic Speech Recognition," Speech Technologies. doi:10.5772/16863. ISBN 978-953-307-996-7; and Lakshmi et al., 2016, "2016 IEEE 6th International Conference on Advanced Computing (IACC)," pp. 31-34. doi:10.1 109/IACC.2016.16, ISBN 978-1-4673-8286-1, each of which is hereby incorporated by reference. Accordingly, in some embodiments, the dimension reduction is a principal component analysis (PCA) algorithm, and each respective extracted dimension reduction component comprises a respective principal component derived by the PCA. In such embodiments, the number of principal components in the plurality of principal components can be limited to a threshold number of principal components calculated by the PCA algorithm. The threshold number of principal components can be, for example, 5, 10, 20, 50, 100, 1000, 1500, or any other number. In some embodiments, each principal component calculated by the PCA algorithm is assigned an eigenvalue by the PCA algorithm, and the corresponding subset of the first plurality of extracted features is limited to the threshold number of principal components assigned the highest eigenvalues. For each respective cellular-component vector in the first and second plurality of cellular-component vectors 130, the plurality of dimension reduction components are applied to the respective cellular-component vector to form a corresponding dimension reduction vector that includes a dimension reduction component value for each respective dimension reduction component in the plurality of dimension reduction components (e.g., forms Matrix M of FIG. 3). This forms a corresponding first and second plurality of dimension reduction vectors. Furthermore, in some embodiments, the method includes performing clustering to generate a set of clusters $C_j$ (e.g., clustering 340 of FIG. 3). Each cluster includes a plurality of points corresponding to a subset of the first and second plurality of dimension reduction vectors. The first plurality of cells from a first cluster of the set of clusters $C_j$ and the second plurality of cells from a second cluster of the set of clusters $C_j$ are both identified.

In some embodiments, the method 200 includes performing manifold learning (e.g., manifold learning 330 of FIG. 3) with the corresponding first and second plurality of dimension reduction vectors 130. This manifold learning identifies a relative cell state of each cell with respect to each other cell in the first and second plurality of cells (e.g., generates Matrix N of FIG. 3). For manifold learning, see, for example, Wang et al., 2004, "Adaptive Manifold Learning," Advances in Neural Information Processing Systems 17, which is hereby incorporated by reference.

In some embodiments, the plurality of unperturbed cells are control cells (e.g., cells that have not been exposed to the perturbation). Furthermore, in some embodiments, the unperturbed cells are an average taken over unrelated perturbed cells that have been exposed to the perturbation.

In some embodiments, the method includes pruning the single-cell transition signature and/or the perturbation signature. This pruning limits the plurality of cellular-components 132 (e.g., limits the cellular components to transcription factors).

In some embodiments, the measure of differential cellular-component expression (e.g., differentially expressed cellular-components 350 of FIG. 3) quantifies a difference in cellular-component quantities between a third plurality of third single-cell cellular-component expression datasets and a fourth plurality of fourth single-cell cellular-component expression datasets. Similarly, in some embodiments this different is determined using one of a difference of means test, a Wilcoxon rank-sum test, a t-test, a logistic regression, or a generalized linear model. Furthermore, each respective third single-cell cellular-component expression dataset 122 in the third plurality of third single-cell cellular-component expression datasets is obtained from a corresponding single cell of in the plurality of unperturbed cells. Moreover, each respective fourth single-cell cellular-component expression dataset in the fourth plurality of fourth single-cell cellularity component expression datasets is obtained from a corresponding single cell of a fourth plurality of cells in the plurality of perturbed cells exposed to the perturbation.

In some embodiments, determining the corresponding second significance score for a respective cellular-component includes replacing the significance score for the respective cellular-component with a corresponding matching score for the respective cellular-component (e.g., replace significance score 134-1-1 associated with cellular component 132-1-1 with significance score 134-$d$-E of FIG. 1) for each respective cellular-component in the plurality of cellular-components. In some embodiments, this replacement forms matching scores. The matching scores combined for the plurality of cellular-components to generate a matching score for the perturbation. Accordingly, whether the perturbation is associated with the transition of cells between the first cell state and the altered cell state (e.g., affects the cell transition) is determined based on the matching score for the respective perturbation. In some embodiments, the matching score includes a discrete score or a continuous score.

In some embodiments, replacing the score 134 includes replacing the significance score with a first score if the cellular-component quantity 132 from the single-cell transition signature 142 for the respective cellular-component and the cellular-component quantity 132 from the perturbation signature 150 for the respective cellular-component are both up-regulated. This replacing further includes replacing the significance score 132 with a second score if the cellular-component quantity from the single-cell transition signature 142 for the respective cellular-component is up-regulated and the cellular-component quantity from the perturbation signature 150 for the respective cellular-component is down-regulated. Moreover, the significance score is replaced with a third score if the cellular-component quantity from the perturbation signature 150 for the respective cellular-component is not significantly up-regulated or down-regulated.

Block 206. Referring to block 206, the method 200 includes comparing the single-cell transition signature 142-1 and the perturbation signature 150-1. This comparison determines whether the perturbation will affect the cellular transition.

In some embodiments, the method 200 includes filtering the single-cell transition signature 142 and/or the perturbation signature 150. This filtering reduces a number of cellular-components 132 included in the single-cell transition signature 142 and the perturbation signature 150, which assists in reducing a data size of the signatures and an amount of time required to conduct the method 200 (e.g., conduct post processing 360 of FIG. 3).

Figure 3:
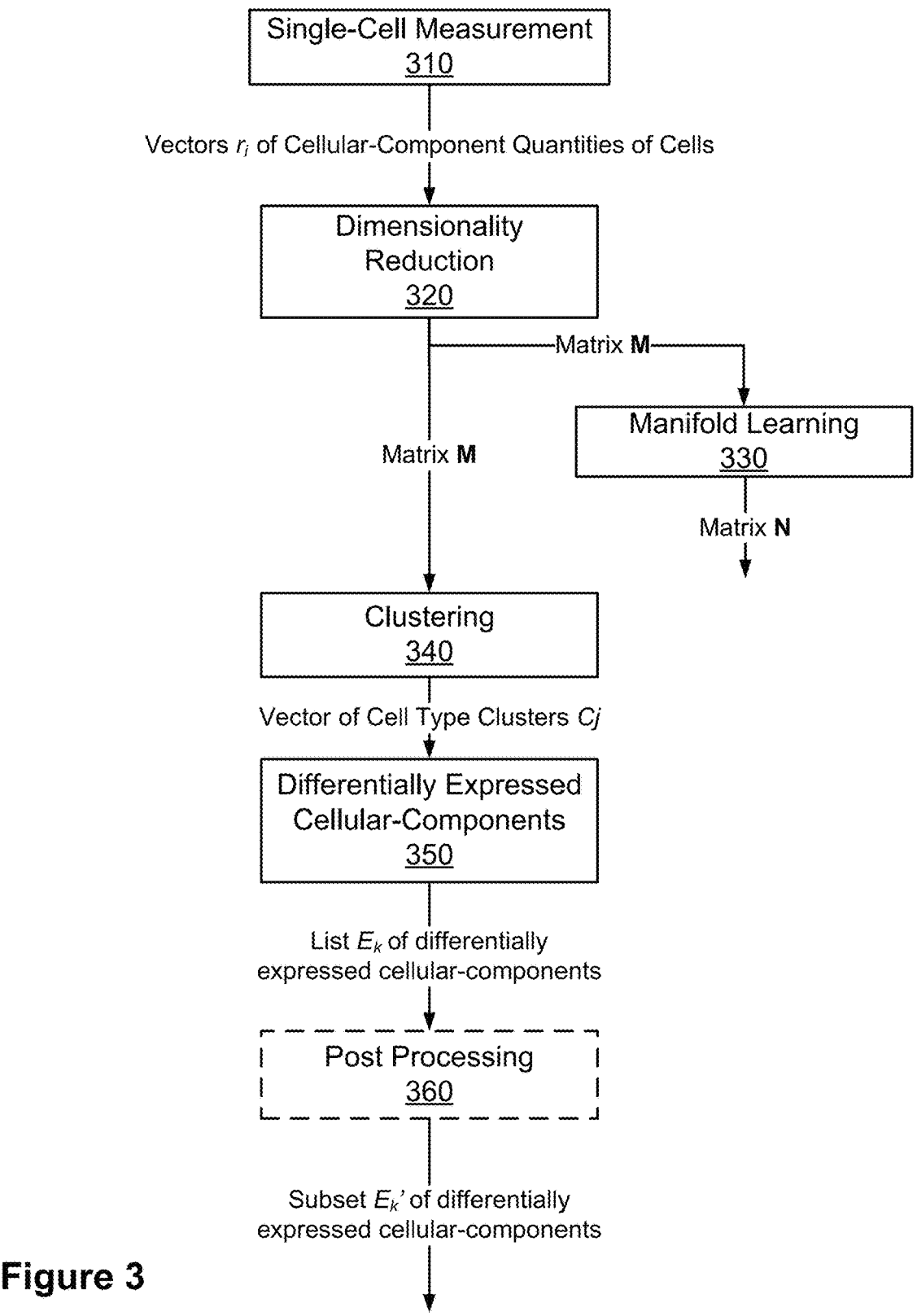
FIG. 3 is a flow chart for a first example of a differential cellular-component expression assay to determine a set of differentially expressed cellular-components, in accordance with an embodiment of the present disclosure.

In some embodiments, the method 200 includes identifying the perturbation as one that promotes the altered cell stated based on the comparing 206 (e.g., based on post processing 360 of FIG. 3). In some embodiments, the single-cell transition signature 142 and/or the perturbation signature 150 are generated using different types of cellular-components. Similarly, in some embodiments, the single-cell transition signature 142 and/or the perturbation signature 150 are generated using the same types of cellular-components.

II. Methods of Culturing Cells In vitro to Perform Single-Cell Analyses

In carrying out the techniques described herein for identifying the causes of cell fate, it is useful to generate datasets regarding cellular-component measurements obtained from single-cells. To generate these datasets (e.g., generate dataset 122-1 of FIG. 1 via single-cell measurement 310 of FIG. 3), a population of cells of interest is cultured in vitro. Single-cell measurements of one or more cellular-components 132 of interest are performed at one or more time periods during the culturing to generate the datasets 122. (e.g., single-cell measurement 310 of FIG. 3). In some embodiments, cellular-components of interest include nucleic acids, including DNA, modified (e.g., methylated) DNA, RNA, including coding (e.g., mRNAs) or non-coding RNA (e.g., sncRNAs), proteins, including post-transcriptionally modified protein (e.g., phosphorylated, glycosylated, myristilated, etc. proteins), lipids, carbohydrates, nucleotides (e.g., adenosine triphosphate (ATP), adenosine diphosphate (ADP) and adenosine monophosphate (AMP)) including cyclic nucleotides such as cyclic adenosine monophosphate (cAMP) and cyclic guanosine monophosphate (cGMP), other small molecule cellular-components such as oxidized and reduced forms of nicotinamide adenine dinucleotide (NADP/NADPH), and any combinations thereof. In some embodiments, the cellular-component measurements include gene expression measurements, such as RNA levels.

Any one of a number of single-cell cellular-component expression measurement techniques may be used to collect the datasets 122 (e.g., techniques of Table 1, techniques of single-cell measurement 310 of FIG. 1, etc.). Examples include, but are not limited to single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and so on. The cellular-component expression measurement can be selected based on the desired cellular-component to be measured. For instance, scRNA-seq, scTag-seq, and miRNA-seq measure RNA expression. Specifically, scRNA-seq measures expression of RNA transcripts, scTag-seq allows detection of rare mRNA species, and miRNA-seq measures expression of micro-RNAs. CyTOF/SCoP and E-MS/Abseq measure protein expression in the cell. CITE-seq simultaneously measures both gene expression and protein expression in the cell, and scATAC-seq measures chromatin conformation in the cell. Table 1 below provides links to example protocols for performing each of the single-cell cellular-component expression measurement techniques described above.

TABLE 1

Example Measaurement Protocols

| Technique | Protocol |
| --- | --- |
| RNA-seq | Olsen et al., (2018), "Introduction to Single-Cell RNA Sequencing," Current protocols in molecular biology 122(1), pg. 57. |
| Tag-seq | Rozenberg et al., (2016), "Digital gene expression analysis with sample multiplexing and PCR duplicate detection: A straightforward protocol," BioTechniques, 61(1), pg. 26. |
| ATAC-seq | Buenrostro et al., (2015), "ATAC-seq: a method for assaying chromatic accessibility genome-wide," Current protcols in molecular biology, 109(1), pg. 21. |
| miRNA-seq | Faridani et al., (2016), "Single-cell sequencing of the small-RNA transcriptome," Nature biotechnology, 34(12), pg. 1264. |
| CyTOF/ SCoPE-MS/ Abseq | Bandura et al., (2009), "Mass cytometry: technique for real time single cell multitarget immunoassay based on inductivitely coupled plasma time-of-flight mass spectrometry," Analystic chemistry, 81(16), pg. 6813. Budnik et al., (2018), "SCoPE-ME: mass scpectrometry of single mammalian cells quantifies proteome heterogenity during cell differentiation," Genome biology, 19(1), pg. 161. Shahi et al., (2017), "Abseq: Ultrahigh-throughoutput single cell protein profiling with droplep microfluidic barcoding," Scientific reports, 7, pg. 44447. |
| CITE-seq | Stoeckius et al., (2017), "Simultaneous epitope and transcritome measurement in single cells," Nature Methods, 14(9), pg. 856. |

The cellular-component expression measurement technique used may result in cell death. Alternatively, cellular-components may be measured by extracting out of the live cell, for example by extracting cell cytoplasm without killing the cell. Techniques of this variety allow the same cell to be measured at multiple different points in time.

If the cell population is heterogeneous such that multiple different cell types that originate from a same "progenitor" cell are present in the population, then single-cell cellular-component expression measurements can be performed at a single time point or at relatively few time points as the cells grow in culture. As a result of the heterogeneity of the cell population, the collected datasets 122 will represent cells of various types along a trajectory of transition.

If the cell population is substantially homogeneous such that only a single or relatively few cell types, mostly the "progenitor" cell of interest, are present in the population, then single-cell cellular-component expression measurements can be performed multiple times over a period of time as the cells transition.

A separate single-cell cellular-component expression dataset 122 is generated for each cell, and where applicable at each of the time periods (e.g., time period 128 of FIG. 1). The collection of single-cell cellular-component expression measurements from a population of cells at multiple different points in time can collectively be interpreted as a "pseudo-time" representation of cell expression over time for the cell types originating from the same "progenitor" cell. The term pseudo-time is used in two respects, first, in that cell state transition is not necessarily the same from cell to cell, and thus the population of cell provides a distribution of what transition processes a cell of that "progenitor" type is likely to go through over time, and second, that the cellular-component expression measurements of those multiple cell's expressions at multiple time points simulates the possible transition behavior over time, even if cellular-component expression measurements of distinct cells give rise to the datasets. As a deliberately simple example, even if cell X gave a dataset for time point A and cell Y gave a dataset for time point B, together these two datasets represent the pseudo-time of transition between time point A and time point B.

For convenience of description, two such datasets 122 captured for a "same" cell at two different time periods (e.g., a first time period 128-1 of first dataset 122-1, a second time period 128-2 of second dataset 122-2, etc.) (assuming a technique is used that does not kill the cell as introduced above) are herein referred to as different "cells" (and corresponding different datasets) because in practice such cells will often be slightly or significantly transitioned from each other, in some cases having an entirely distinct cell type as determined from the relative quantities of various cellular-components. Viewed from this context, these two measurements of a single-cell at different time points can be interpreted as different cells for the purpose of analysis because the cell itself has changed.

Note that the separation of datasets by cell (e.g., cell/dataset identifier 126 of FIG. 1)/time period (e.g., time period 128 of FIG. 1) described herein is for clarity of description, in practice, these datasets may be stored in computer memory and logically operated on as one or more aggregate datasets (e.g., by cell for all time periods, for all cells and time periods at once).

In some embodiments, it is useful to collect datasets 122 where a "progenitor" cell of interest has been perturbed from its base line state. There are a number of possible reasons to do this, for example, to knock out (e.g., remove, nullify, etc.) one or more cellular-components, to evaluate the difference between healthy and diseased cell states, etc. In these embodiments, a process may also include steps for introducing the desired modifications to the cells. For example, one or more perturbations may be introduced to the cells, tailored viruses designed to knock out one or more cellular-components may be introduced, CRISPR may be used to edit cellular-components, and so on. Examples of techniques that could be used include, but are not limited to, RNA interference (RNAi), Transcription activator-like effector nuclease (TALEN), or Zinc Finger Nuclease (ZFN).

Depending upon how the perturbation is applied, not all cells will be perturbed in the same way. For example, if a virus is introduced to knockout a particular gene, that virus may not affect all cells in the population. More generally, this property can be used advantageously to evaluate the effect of many different perturbations with respect to a single population. For example, a large number of tailored viruses may be introduced, each of which performs a different perturbation such as causing a different gene to be knocked out. The viruses will variously infect some subset of the various cells, knocking out the gene of interest. Single-cell sequencing, or another technique can then be used to identify which viruses affected which cells. The resulting differing single-cell sequencing datasets can then be evaluated to identify the effect of gene knockout on gene expression in accordance with the methods described elsewhere in this description.

Other types of multi-perturbation cell modifications can be performed similarly, such as the introduction of multiple different perturbations, barcoding CRISPR, etc. Further, more than one type perturbation may be introduced into a population of cells to be analyzed. For example, cells may be affected differently (e.g., different viruses introduced), and different perturbations may be introduced into different sub-populations of cells.

Additionally, different subsets of the population of cells may be perturbed in different ways beyond simply mixing many perturbations and post-hoc evaluating which cells were affected by which perturbations. For example, if the population of cells is physically divided into different wells of a multi-well plate, then different perturbations may be applied to each well. Other ways of accomplishing different perturbations for different cells are also possible.

Below, methods are exemplified using single-cell gene expression measurements. It is to be understood that this is by way of illustration and not limitation, as the present invention encompasses analogous methods using measurements of other cellular-components obtained from single-cells. It is to be further understood that the present invention encompasses methods using measurements obtained directly from experimental work carried out by an individual or organization practicing the methods described in this disclosure, as well as methods using measurements obtained indirectly, e.g., from reports of results of experimental work carried out by others and made available through any means or mechanism, including data reported in third-party publications, databases, assays carried out by contractors, or other sources of suitable input data useful for practicing the disclosed methods.

As discussed herein, gene expression in a cell can be measured by sequencing the cell and then counting the quantity of each gene transcript identified during the sequencing. In some embodiments, the gene transcripts sequenced and quantified may include RNA, for example mRNA. In alternative embodiments, the gene transcripts sequenced and quantified may include a downstream product of mRNA, for example a protein such as a transcription factor. In general, as used herein, the term "gene transcript" may be used to denote any downstream product of gene transcription or translation, including post-translational modification, and "gene expression" may be used to refer generally to any measure of gene transcripts.

Although the remainder of this description focuses on the analysis of gene transcripts and gene expression, all of the techniques described herein are equally applicable to any technique that obtains data on a single-cell basis regarding those cells. Examples include single-cell proteomics (protein expression), chromatin conformation (chromatin status), methylation, or other quantifiable epigenetic effects.

The following description provides an example general description for culturing a population of cells in vitro in order to carry out single-cell cellular-component expression measurement (e.g., measurement 310 of FIG. 3) over multiple time periods (e.g., a plurality of time periods 128 of FIG. 1). Generally, methods for culturing cells in vitro are known to those of skill in the art. Those of skill in the art will also appreciate how this process could be modified to grow for longer or shorter periods, conduct additional or fewer single-cell measurement steps, and so on.

In one embodiment, the process for culturing cells in a first cell state into cells in an altered cell state includes one or more of the following steps:

Day 0: Thaw a number of cells in the first cell state onto a plate in a media suitable for growth of the cells.

Day 1: Seed some number of cells in the first cell state into a multi-well plate. If applicable, perform additional steps to affect cellular-components of cells. For example, simultaneously infect with one or more viruses to knockout cellular-components of interest.

Perform cellular-component expression measurement iteration $t_1$ for cells in the wells.

Day 1+l: Change media as needed if any additional processes were performed.

If applicable, perform cellular-component expression measurement iteration $t_1$ for cells in the wells.

Day 1+m: Change media to media appropriate to support growth of cells in the altered cell state.

If applicable, perform cellular-component expression measurement iteration $t_m$ for cells in the wells.

Days 1+n, o, p, etc.: Media change as needed to support further cell state transition from the first cell state to the altered cell state. If applicable, perform additional steps to affect further transition from the first cell state to the altered cell state. For example, add perturbations of interest to push cells towards the altered cell state.

If applicable, perform cellular-component expression measurement iterations $t_n$, $t_o$, $t_p$, etc., for cells in the wells.

Day q: Perform cellular-component expression measurement iteration $t_q$ for cells in the altered cell state in the wells.

Fix plate and stain with antibodies matched to cellular-components/proteins of interest to sort/identify cells without having to lyse/destroy them to be measured. It also can be used to identify surface markers that might not be seen with as much resolution in the setting of the cytoplasm. Image with a cell imaging system such as the Molecular Devices HCI IXM4 by scanning each well. Quantify of number of cells per well that are in the desired altered cell state.

Table 2 illustrates a snippet of a number of datasets 122, including example data that might be collected from single-cell expression measurement of a population of cells at one or more points in time (e.g., single-cell measurement 310 of FIG. 3). The sample ID column indicates which sample a cell's data came from (e.g., sample identifier 124-1 of FIG. 1). In practice, the cells in the population may be drawn from more than one sample (e.g., first sample identifier 124-1, second sample identifier 124-2, etc.), each of which may have originated from the same or a different subject. The cell or dataset column indicates which cell or dataset a given row's data is associated with (e.g., cell/dataset identifier 126-1 of FIG. 1). The dataset 122 may alternatively be represented as a vector of data $r_i$ (e.g., cellular-component vector 130-1 of FIG. 1). The time period column indicates when during the growth of the cell the dataset of that row was captured, if relevant (e.g., time period 128-1 of FIG. 1).

The remaining columns of Table 2 correspond to the cellular-components of interest of the cell (cellular-component 132-1-1 through 132-1-B). This may be all cellular-components of the cell, or merely a subset. Each cellular-component 132 is associated with a different column. If the dataset is represented as a vector $r_i$, each cellular-component corresponds to an entry i in the vector. In some embodiments, the value of each cell can be an (integer) count of a number of the cellular-component as measured by single-cell expression measurement, or some normalized (rational number) version thereof.

compressed down to a lower dimensional space while preserving the shape of whatever latent information is encoded in the datasets (e.g., cellular component vector 130 of FIG. 1 dimensionality reduced 320 to Matrix M of FIG. 3). The low dimensional data is evaluated to identify differentially present cellular-components between different stages of cell state transition. As the input data to the method is single-cell cellular-component expression datasets 122 of multiple cellular-components of interest on a per-cell basis, the set of differentially expressed cellular-components therefore represents which cellular-components had statistically significant over- or under-representation in terms of presence, absence or amounts relative to other cellular-components of the cells. Any one of a number of methods and metrics may be used to identify which of those cellular-components are sufficiently "differently" expressed relative to other cellular-components so as to be tagged as "differentially expressed" in accordance with this description. As the population of cells from which the datasets 122 may be obtained includes

TABLE 2

Example Datasets

| Sample ID | Cell/ Dataset r | Time Period | Cellular-component 1 0610005C13Rik | Cellular-component 2 0610007C21Rik | Cellular-component 3 0610007L01Rik |
|---|---|---|---|---|---|
| ID1 | 1_iN1_C01 | $t_0$ | 0 | 0 | 0 |
| ID1 | 1_iN1_C02 | $t_0$ | 0 | 7.377047 | 0 |
| ID1 | 1_iN1_C03 | $t_1$ | 0 | 0 | 3.544937 |
| ID2 | 1_iN1_C04 | $t_1$ | 0 | 3.926875 | 0 |
| ID2 | 1_iN1_C05 | $t_2$ | 0 | 6.39981 | 6.946602 |
| ID2 | 1_iN1_C07 | $t_2$ | 0 | 7.995805 | 2.724768 |

III. Methods of Analyzing Single-cell Datasets to Determine Differential Expression of Cellular-components III.A. Overview Cell state transitions (i.e., a transition in a cell's state from a first cell state to an altered cell state) are marked by a change in expression of cellular-components 132 in the cell. For example, a transition can be marked by a change in cellular-component expression 132 in the cell, and thus by the identity and quantity cellular-components (e.g., mRNA, transcription factors) produced by the cell. At least currently, however, cell state transition is not entirely deterministic, due to the complexity of intracellular activity. To attempt to gain insight into this complexity, this description applies statistical techniques to single-cell datasets 122 quantifying cellular-components 132 in a cell of a population of cells under the theory that varying cellular-component expression, associated with varying presence, absence or amounts of one or more measured cellular-components of interest, at different stages in cell state transition provides a high dimensional dataset (e.g., cellular-component vector 130 of FIG. 1) from which meaningful knowledge can be extracted. Here, the high dimensionality of the data originates from the per-cellular-component measurements contained in the datasets 122. Each cellular-component 132 represents a dimension, and collectively the cellular-component measurement dataset 122 for each cellular-component may have a shape which encodes latent information about biological processes regarding the transition of "progenitor" cells into different cell types. In practice, the number of cellular-components 132 may be on the order of thousands to tens of thousands, making the computations described herein impractical if not impossible to perform mentally or by hand.

Generally, these statistical techniques can be characterized as methods in which the high dimensional data is cells of different types and different stages of transition, knowing which cellular-components are differentially present (e.g., which cellular-components were differentially expressed) provides insight into what cellular-components impact or associate with expression of cellular-components that are active in the process of transition or other transitions.

III.B. Use Cases

Regardless of which class of method is used, the determination of the differentially expressed cellular-components may vary depending upon what result is sought. For example, if the method used identifies particular cells as being on-lineage or off-lineage, the determination of which cellular-components are differentially expressed may be performed by comparing the expression levels of cellular-components of cells determined to be on-lineage to the cellular-components of cells determined to be off-lineage. The relative expression of those cellular-components indicates which cellular-components, individually or in combination, are active in cells of one type or another. As above, this expression data can be used to identify a subset of cellular-components to be flagged as differentially expressed. Causality may then be determined by knocking out identified cellular-components in vitro and evaluating whether or not cell fate of experimental cell populations is affected by the changes in which cellular-components are active.

As another example, if the method used identifies particular cells as being on-lineage, and other cells as being "progenitor" cells or intermediate cells along a transition trajectory towards the on-lineage cell type, the determination of which cellular-components are differentially expressed may be performed by comparing the expression levels of cellular-components of cells determined to be on-lineage to the cellular-components of cells determined to be "progenitor" and/or intermediate cells of the on-lineage cells. As in the prior paragraph, the relative expression of those cellular-components indicates which cellular-components, individually or in combination, are active in cells of one type or another, and again this expression data can be used to identify a subset of cellular-components to be flagged as differentially expressed. Also as above, causality may then be determined by knocking out identified cellular-components in vitro and evaluating whether or not cell fate of experimental cell populations is affected by the changes in which cellular-components are active.

As another example, the population of cells may include two sub-populations of cells, one healthy sub-population and one unhealthy sub-population. During cell culturing, a plurality of different perturbations may be introduced into the unhealthy sub-population. Through subsequent single-cell expression measurement in conjunction with the methods described herein, it can be determined what effect the perturbations had in the differential cellular-component expression of the cellular-components in the unhealthy sub-population, particularly in related to the healthy sub-population. For example, a subset of the cells from the un-healthy sub-population exposed to one or more perturbations may exhibit cellular-component expression consistent with the healthy sub-population of cells, indicating that the perturbation had a desirable effect on the un-healthy sub-population of cells.

III.C. Determining Differentially Expressed Cellular-components Using Low Dimensional Data FIG. 3 is a flow chart for a first example of a differential cellular-component expression assay to determine a set of differentially expressed cellular-components 132, according to one embodiment. Note FIG. 3 provides a non-limiting, illustrative embodiment of the general case described using differential cellular-component expression. At step 310, a single-cell expression measurement, as discussed in Section II above, is performed to generate a plurality of datasets 122 for a population of cells. As above, each dataset 122 for each cell may be represented as a vector $r_i$ of cellular-components (e.g., cellular-component vector 130 of FIG. 1) including quantities for each of l cellular-components (e.g., cellular-components 132-1-1 through 132-1-B of FIG. 1). The datasets 122 obtained from single-cell expression measurement 310 are generally stored in a digital format in a persistent memory (e.g., persistent memory 112 of FIG. 1) of a computing device (e.g., system 100 of FIG. 1), however they may be loaded into active memory (e.g., non-persistent memory 111 of FIG. 1) as needed in order to carry out the remaining steps described herein. Generally, the remaining steps of the process of FIG. 3 are carried out by one or more computing devices (e.g., system 100 of FIG. 1). An example computing device is discussed with respect to FIG. 1. However, in practice the process of FIG. 3 may contain additional interstitial or follow on steps that may be conducted outside of a computer, such as additional in vitro tests or clinical decisions carried out on the basis of the outcomes of the steps described herein.

III.C.1. Dimensionality Reduction

As introduced above, as each of the cellular-components 132 represent a different dimension of data, the datasets 122 have, in total, a high-dimensionality. At step 320, a dimensionality reduction is performed by the computing device (e.g., system 100) to reduce the dimensionality of the data while preserving the structure of any latent patterns that are present in the cellular-component 132 quantities of the datasets 122.

The input to the dimensionality reduction step 320 is generally a matrix, similar to Table 2 above, that concatenates the expression vectors of the individual cells (e.g., cellular-component vector 130 of FIG. 1). The output of the dimensionality reduction 320 is a matrix, herein referred to as matrix "M" for simplicity, which encodes the original data in a compressed form while maintaining the underlying latent structure of the data. Each row in the matrix M is associated with a particular one of the cells. Each column in the matrix M is associated with one of the dimensions in the reduced dimensional space provided by the dimensionality reduction. The values in the entries at each row-column grouping are determined by the dimensionality reduction based on the original input datasets.

In some embodiments, these dimensionality reduction techniques result in some lossy compression of the data, however the resulting output matrix M is smaller in computational storage size, and therefore requires less computing processing power to analyze with other downstream techniques discussed in the remaining steps of this process, which makes it computationally feasible to obtain the results of those steps in a reasonable time with computing devices of the current era.

A variety of dimensionality reduction techniques may be used. Examples include, but are not limited $t_o$, principal component analysis (PCA), non-negative matrix factorization (NMF), linear discriminant analysis (LDA), diffusion maps, or (neural) network techniques such as an autoencoder.

Each of the techniques mentioned in these paragraphs operates differently to extract the main drivers of variation and reduce the dimensionality of the original input data, but each outputs a matrix M in a lower dimensional space.

III.C.2. Manifold Learning

The reduced dimensionality data in matrix M (e.g., dimension reduction components store 146) is reduced in dimensionality significantly relative to the original high dimensional data from the single-cell expression datasets 122. However, the resulting matrix M embeds a non-linear manifold (e.g., manifold 149 of FIG. 1). At step 330, a manifold learning technique is applied to the matrix M to extract the manifold. Not only does the manifold 149 itself provide useful information about differential cellular-component expression amongst cells over pseudo-time, it can also be used to visualize that information.

The input to the manifold learning step 330 is matrix M from the dimensionality reduction step 320. The output of the manifold learning 330 is another matrix, herein referred to as matrix "N" or as a/the manifold (e.g., manifold 149 of FIG. 1). The structure of matrix N is such that each row of matrix N corresponds to one of the original cells of the population, herein referred to as 'points' for the remaining steps of this process. In one embodiment, matrix N has two columns, arbitrarily referred to as an X dimension and a Y dimension, corresponding to the two dimensions the manifold learning step 330 is configured to output, independent of the specific manifold learning algorithm used. The X and Y dimensions are determined by the manifold learning steps, and are chosen according to which dimensions best fit the data from matrix M according to which manifold algorithm is used. A manifold with two such columns is convenient for visualization, as illustrated in FIG. 4B. In other embodiments, the manifold matrix N has additional dimensions beyond the two-dimensional version introduced herein.

An example matrix N is provided in Table 3 below. FIG. 4B provides a plot of the data from example 1 below, in an embodiment where force directed layout is used in the dimensionality reduction step. The plot in FIG. 4B is exemplary of the results achieved in accordance with this process, in that in this and similar example experiments, the points separate in the X/Y dimensions along one or more trajectories in the X/Y plane, where generally "progenitor" cells appear in one general region in X/Y space, diffusing towards intermediate cells at another general region in X/Y space, and ending at one or more different regions in X/Y space, which in practice are generally validated as being on- or off-lineage transitioned cells. Generally, the number of regions and trajectories identified depends on the type of "progenitor" cell and the types of cells the "progenitor" cells are known to transition into. Further, the regions of points often have some amount of diffusion between them, suggesting cells in different stages of progression in the process of transition.

TABLE 3

| Output Matrix N | | |
| --- | --- | --- |
| Points (Cells) | X Dimension | Y Dimension |
| Point 1 | $x_1$ | $y_1$ |
| Point 2 | $x_2$ | $y_2$ |
| Point 3 | $x_3$ | $y_3$ |
| Point 4 | $x_4$ | $y_4$ |
| ... | ... | ... |
| Point p | $x_p$ | $y_5$ |

A variety of manifold learning techniques may be applied to the matrix M to generate matrix N. Examples include, but are not limited $t_o$, force-directed layout (Fruchterman, T. M., & Reingold, E. M. (1991). Graph drawing by force-directed placement. *Software: Practice and experience*, 21(11), 1129-1164) (e.g., Force Atlas 2), t-distributed stochastic neighbor embedding (t-SNE), locally linear embedding (Roweis, S. T., & Saul, L. K. (2000). Nonlinear dimensionality reduction by locally linear embedding. *Science*, 290(5500), 2323-2326), local linear isometric mapping (ISOMAP, Tenenbaum, J. B., De Silva, V., & Langford, J. C. (2000). A global geometric framework for nonlinear dimensionality reduction. *Science*, 290(5500), 2319-2323), kernel PCA, graph-based kernel PCA, Potential of Heat-Diffusion for Affinity Based Trajectory Embedding (PHATE), generalized discriminant analysis (GDA), Uniform Manifold Approximation and Projection (UMAP), or kernel discriminant analysis. Discriminant analysis may be used particularly where some information is known in advance as to the specific cell type of each cell. Force-directed layouts are useful in various particular embodiments because of their ability to identify new, lower dimensions that encode nonlinear aspects of the underlying data which arise from underlying biological processes like cell state transition. Force directed layouts use physics-based models as mechanisms for determining a reduced dimensionality that best represents the data. As an example, a force directed layout uses a form of physics simulation in which, in this embodiment, each cell/dataset in the set is assigned a "repulsion" force and there exists a global "gravitation force" that, when computed over the entirety of cells, identifies sectors of the data that "diffuse" together under these competing "forces." Force directed layouts make few assumptions about the structure of the data, and do not impose a de-noising approach.

Note that performing manifold learning 330 is an optional step. In some embodiments, manifold learning is not performed.

III.C.3. Clustering

At step 340, clustering is performed to generate a set of j clusters $C_j$ in order to identify patterns in locations of the points in the low dimensional space provided by dimensionality reduction 320 (e.g., corresponding to a subset of the associated plurality of dimension reduction vectors 146). These clusters are used to aggregate similar points (cells/datasets) to draw out statistically relevant information about groups of points (e.g., a first cluster, a second cluster, etc.) that are similar to each other in the low dimensional space. Table 4 below illustrates an example clustering of points that may be the output of clustering 340.

TABLE 4

| Cluster Assignments | |
| --- | --- |
| Cells/ Points | Cluster Assignment $C_j$ |
| Point 1 | $C_1$ |
| Point 2 | $C_1$ |
| Point 3 | $C_1$ |
| Point 4 | $C_2$ |
| Point 5 | $C_2$ |
| Point 6 | $C_2$ |

Any one of a number of clustering techniques can be used, examples of which include, but are not limited $t_o$, hierarchical clustering, k-means clustering, and density based clustering. In one specific embodiment, a hierarchical density based clustering algorithm is used (referred to as HDB-SCAN, Campello, R. J., Moulavi, D., Zimek, A., & Sander, J. (2015). Hierarchical density estimates for data clustering, visualization, and outlier detection. *ACM Transactions on Knowledge Discovery from Data* (TKDD), 10(1), 5). In another embodiment, a community detection based cluster algorithm is used, such as Louvain clustering (Blondel, V. D., Guillaume, J. L., Lambiotte, R., & Lefebvre, E. (2008). Fast unfolding of communities in large networks. *Journal of statistical mechanics: theory and experiment*, 2008(10), P10008).

Figure 7A:
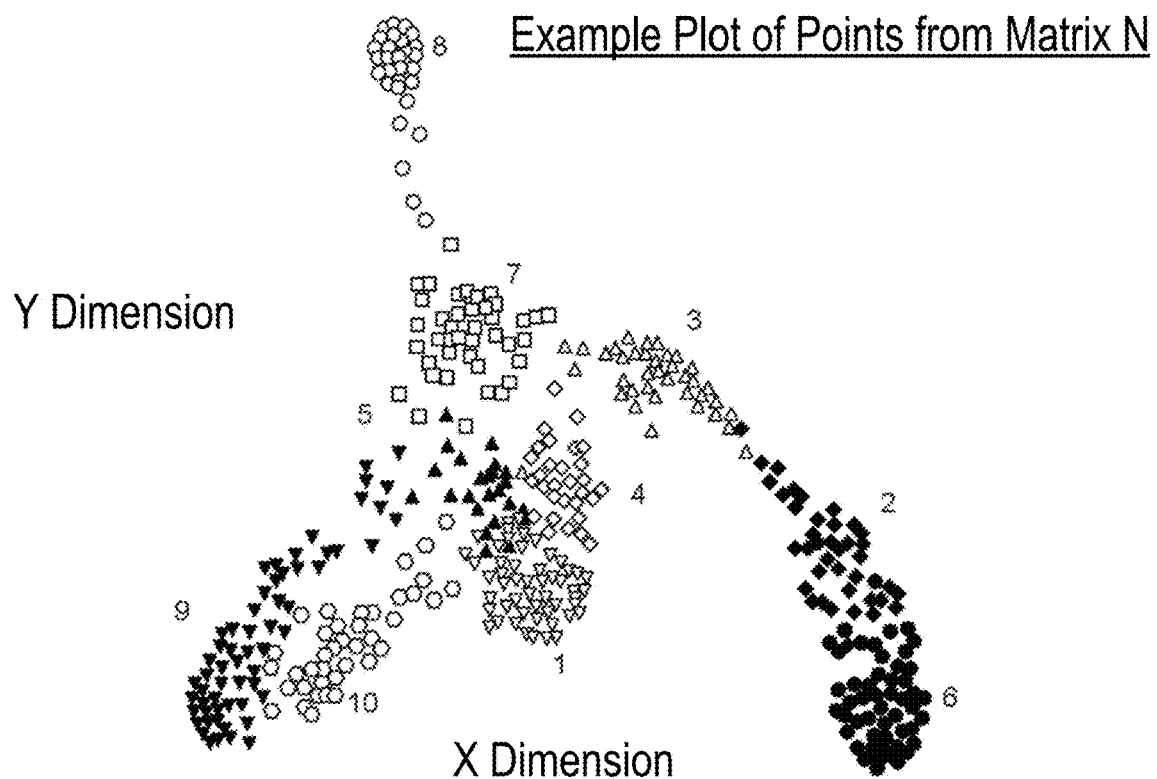
FIG. 7A depicts the manifold of FIG. 4B, with the points in the manifold grouped into clusters $C_j$ identified by clustering, in accordance with an embodiment of the present disclosure.

For clustering, these techniques use the data of the matrix M to determine the clusters. Independent of algorithm, generally points closer to each other in the multi-dimensional space of the matrix M are more likely to be assigned to the same cluster, and points that are further away from each other are less likely to be assigned to the same cluster. FIG. 7A, provides a plot of the example data from FIG. 4B with cluster assignments 1-10 indicated with different visual markers to each of the points. The number of clusters may be set or constrained by the operator and/or determined dynamically based on the algorithm used.

III.C.4. Determining Differential Cellular-component Expression

The dimensionality reduction 320, optional manifold learning 330, and clustering 340 steps generally operate to organize the cells of the population, and their corresponding single-cell expression datasets 122, into clusters within a reduced dimension space so that the underlying per cellular-component expression measurement data can be aggregated and analyzed to extract meaningful information. In some embodiments, this reduced dimension space furthers reduces an amount of time and/or processing power required to complete the methods of the present disclosure.

One item of information which can be obtained from the clusters is which of the cellular-components are differentially expressed in the population relative to which other cells. Herein, this set of cellular-components is referred to as a set of differentially expressed cellular-components $E_k$, discussed in FIG. 3 at step 350. Some example use cases for generating the set of differentially expressed cellular-components are discussed in Section IIIB. above.

There are a number of ways to use the cluster $C_j$ and dataset information to determine the set of differentially expressed cellular-components. In one embodiment, the determination of whether a given cellular-component (e.g., cellular-component A) is differentially expressed is determined by evaluating the quantity of cellular-component A by the points (cells) in a given cluster $C_1$ against the quantity of cellular-component A by the points in one or more of the other clusters $C_m$ where m is not equal to 1. Normalizations may also be used. For example, the level of expression by the cellular-components in a cell as a whole may vary cell to cell for reasons that are independent of cell state transition biology. As such, cellular-component quantities may be normalized based on the overall number of cellular-component quantities for each cell in a dataset.

As discussed in Section III.B above, which cluster's cellular-component quantities for cellular-component A are compared against the given cluster $C_1$ may vary by embodiment. The other clusters used for comparison may be a cluster most strongly associated with an on-lineage cell type, most strongly associated with an off-lineage cell type, most associated with a "progenitor" cell type, most associated with an intermediate cell type, etc. Comparisons may also be made against more than one other cluster.

Given the comparison, cellular-component A may be identified as differentially expressed according to any one of a number of metrics, such as total cellular-component quantity per cluster (again, for all points in the cluster, or some aggregate measure such as an average, etc.), normalized cellular-component quantity per cluster, median, average, or other aggregate cellular-component quantity per cluster, proportion of expression relative to cellular-component quantities of other cellular-components, and so on. In one embodiment, the criteria for establishing that cellular-component A is differentially expressed is a threshold requirement.

For example, the normalized cellular-component quantity for cellular-component A in cluster $C_1$ may have exceed the normalized cellular-component quantity for cellular-component A one or more other clusters $C_m$ by at least a threshold.

The determination of differentially expressed cellular-components may also be relative. In one embodiment, normalized cellular-component quantities for multiple cellular-component/cluster combinations, distance metrics for multiple cellular-component/cluster combinations, or other similar metrics may be calculated. Those metrics may be ranked according to a ranking criterion (e.g., highest normalized cellular-component quantity in a cluster), and the top ranked cellular-components or cellular-component/cluster combinations may be determined to be the differentially expressed cellular-components.

In one embodiment, the cellular-component quantities for a given cellular-component in a given cluster may be used identify which cellular-components are differentially expressed. In one embodiment, these differentially expressed cellular-components are identified using one of a difference of means test, a Wilcoxon rank-sum test (Mann Whitney U test), a t-test, a logistic regression, and a generalized linear model Those of skill in the art will appreciate that other metrics are also possible that involve cellular-component quantity per cellular-component/cluster combinations.

III.C.5. Post Processing

The set of differentially expressed cellular-components $E_k$ represent a useful output in their own right. However, it can be useful to further analyze 360 the set of differentially expressed cellular-components to identify a subset of that set.

In one embodiment, the set of differentially expressed cellular-components is screened against a transcription factor database (e.g., signature store 140 of FIG. 1) to identify a set of transcription factors associated with the cellular-components present in the set. As an example, this information may be obtained from ChIP-seq datasets (information about which transcription factors bind to which regions of DNA, which is aligned to cellular-components).

The datasets 122 discussed herein for a particular cell, for example the original input datasets r (e.g., dataset 122-1 of FIG. 1) or the set of different expressed cellular-components $E_k$ and corresponding datasets, may be missing cellular-component quantities for any number of reasons (e.g., technical noise, drop out, low cellular-component quantity, etc.) To account for these and any additional confounding factors, simple models can be fit to the dataset.

III.D. Prediction of Perturbations that Affect Cell State Transition

By matching differential cellular-component expression that characterizes a particular cellular transition to differential cellular-component expression caused by exposure of a cell to a perturbation, perturbations that affect the particular cell state transition can be predicted. A perturbation of a cell includes any treatment of the cell with one or more compounds. The one or more compounds can include, for example, a small molecule, a biologic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other cellular-component editing system), or any combination of any of the foregoing. Differentially expressed cellular-components for a particular cellular transition can be compared with differentially expressed cellular-components caused by exposure of a cell to a perturbation. Then, the perturbations that cause differential cellular-component expression that matches the differential cellular-component expression of the particular cellular transition can be predicted to affect the particular cellular transition.

To predict perturbations that affect a particular cellular transition by matching differential cellular-component expression that characterizes the particular cellular transition to differential cellular-component expression caused by exposure of a cell to a perturbation, first, the most differentially expressed cellular-components that characterize the particular cellular transition are identified. In some embodiments, these differentially expressed cellular-components are identified using one of a difference of means test, a Wilcoxon rank-sum test (Mann Whitney U test), a t-test, a logistic regression, and a generalized linear model. In alternative embodiments, any statistical method may be used to identify the most differentially expressed cellular-components for a particular cellular transition. The resulting ranked table (or list) of cellular-component 132 names and significance scores 134 may also be referred to as the 'single-cell transition signature,' (e.g., includes the single-cell transition signature 142 of FIG. 1). The significance score 134 of each cellular-component 132 quantifies an association between a change in cellular-component expression of the cellular-component and a change in cell type between the original cell type and the transitioned cell type. In aggregate, these scores 134 form an overall measure of the differential cellular-component expression associated with transition between the original cell type (first cell state) and the transitioned cell type (altered cell state).

Similarly, differential cellular-component expression caused by exposure of a cell to a perturbation is identified for one or more perturbations. In some embodiments, to identify differential cellular-component expression caused by exposure of a cell to a perturbation, the cellular-component expression in the cell exposed to the perturbation is compared to the cellular-component expression in control cell(s) that have not been exposed to the perturbation or an average over unrelated perturbed samples (e.g., post processing 360 of FIG. 3). In some embodiments, this comparison is performed using a one of difference of means test, a Wilcoxon rank-sum test (Mann Whitney U test), a t-test, a logistic regression, and a generalized linear model. In alternative embodiments, any statistical method may be used to perform the comparison. In even further alternative embodiments, the differential cellular-component expression caused by exposure of the cell to a perturbation may be known and identified from literature. The resulting analogous ranked table (or list) of cellular-component names and significance scores may be referred to as the 'perturbation signature.'

In some embodiments, to reduce confounding due to technical variation, different experimental assays, and other variables in identification of the single-cell transition signature and the perturbation signature, one or both of the signatures are filtered to include only transcription factors, which are proteins known to drive expression of certain cellular-components. These transcription factors may be identified, for example, from literature.

In some embodiments, to further reduce confounding due to technical variation and ambiguity of cellular transition, the most differentially expressed cellular-components of one or both of the signatures are truncated (or filtered or subsetted) at a given p-value and/or at a threshold number of cellular-components. The resulting a truncated set of differentially expressed cellular-components for the cellular transition and the perturbation exposure are unordered and may contain between 10 and 25 cellular-components, or greater or fewer depending on the implementation.

Following identification and any processing of one or both of the signatures (e.g., single-cell transition signature 142 and/or perturbation signature 150 of FIG. 1), the differentially expressed cellular-components for the single-cell transition signature 142 are compared with the differentially expressed cellular-components for the perturbation signature 150. In one embodiment, to perform the comparison, the differentially expressed cellular-components of the perturbations are represented as a matrix (e.g., Matrix M of FIG. 3, cellular component vector 130 of FIG. 1, etc.). Each row of the matrix is associated with a single perturbation. Each column on the matrix is associated with one of the differentially expressed cellular-components. Each entry in the matrix includes a significance score 134 (e.g., a p-value, a t-score) for a differentially expressed cellular-component 132 identified for a particular perturbation. This matrix is subset to include only the differentially expressed cellular-components that were identified for the single-cell transition signature 142. This filtering may be accomplished using the methods described in the previous paragraph (e.g., by threshold p-value, by threshold number of cellular-components, etc.)

Each significance score 134 in the matrix is replaced with a discrete matching score. To replace each significance score with a discrete matching score, the significantly up-regulated cellular-components 132 for the cellular transition and the significantly down-regulated cellular-components for the cellular transition are identified. For each of the significantly up-regulated cellular-components identified by the single-cell transition signature 142, if the cellular-component is also significantly up-regulated for the perturbation signature 150 for that perturbation, the significance score in the matrix for that cellular-component/perturbation combination is replaced with a discrete matching score of '1'. If the cellular-component is significantly down-regulated for a perturbation signature relative to the single-cell transition signature, the significance score in the matrix for that cellular-component/perturbation combination is replaced with a discrete matching score of '−2'. If the cellular-component is not significantly up-regulated or down-regulated for a perturbation signature, the significance score in the matrix for the cellular-component/perturbation combination is replaced with a discrete matching score of '0'.

Conversely, for each of the significantly down-regulated cellular-components identified in the single-cell transition signature, if the cellular-component is also significantly down-regulated for a perturbation, the significance score in the matrix for that cellular-component/perturbation combination is replaced with a discrete matching score of '−1'. If the cellular-component is significantly up-regulated for a perturbation, the significance score in the matrix for that cellular-component/perturbation combination is replaced with a discrete matching score of '2'. If the cellular-component is not significantly up-regulated or down-regulated for a perturbation, the significance score in the matrix for that cellular-component/perturbation combination is replaced with a discrete matching score of '0'. One of skill in the art will appreciate that these particular score replacements may be substituted with other numerical values in some embodiments.

The result is a matrix with the number of rows given by the number of perturbations and the number of columns given by the differential cellular-components from the single-cell transitions and the entries representing the matching score described above.

Following replacement of the significance scores in the matrix with the discrete matching scores as described above, the discrete matching scores in each row of the matrix are summed to generate a summed matching score for each row. Then, the rows of the matrix, each corresponding to a perturbation, are ranked in order of decreasing summed matching score. The top-ranked rows are associated with the perturbations that are most likely to be associated with the identified cellular transition of the single-cell transition signature.

In some embodiments, for the summed matching score of each row in the matrix, an estimation of the false cellular-component discovery rate is estimated. To estimate the false cellular-component discovery rate, the empirical marginal expression frequency for each cellular-component is calculated, and the empirical marginal expression frequencies are summed for each cellular-component over their combinations, which generates a probability of identifying a given number of cellular-components by chance (how likely it is to observe expression that was at least as rare as was seen in the datasets used to generate the signatures), assuming independently distributed expression. That probability can then be used to compute the false cellular-component discovery rate.

In certain embodiments, covariates of a perturbation may exist. For example, if the perturbations are small molecules, covariates of a small molecule may include, a specific dose of the small molecule, a time at which the cell exposed to the small molecule is measured to quantify cellular-components, and/or the identity (e.g., cell line) of the cell exposed to the small molecule. In some embodiments, a perturbation is predicted to affect a particular cellular transition only when a threshold quantity of its covariates are also predicted to affect the particular cellular transition. For example, a perturbation may be predicted to affect a particular cellular transition only when at least two of its covariates are also predicted to affect the particular cellular transition.

Alternate methods of matching may be used. For example, cellular-components may be matched to a database using a web interface (e.g., such as L1000CDS2. An ultra-fast LINCS L1000 Characteristic Direction Signature Search Engine, on world wide web at amp.pharm.mssm.edu/L1000CDS2/#/index). This method of matching does not perform as well as the method of matching described in prior paragraphs, the latter yields results with much higher sensitivity, scales much better and covers much more data (millions of samples instead of tens of thousands), accounts for significant overlap, discounts for significant inconsistencies and ignores non-significant information in the signatures.

Finding perturbations that match a particular single-cell state transition can be difficult due to highly variable cellular-component expression for a particular single-cell state transition and due to highly variable cellular-component expression affected by perturbations. To mitigate this problem, in some alternative embodiments, the matching and subsequent identification of perturbations that affect cell state transition along a particular trajectory can be performed by a trained neural network model.

An example in which the perturbations are perturbations that affect a particular cell state transition are identified using the above method is provided below in Section IV.E.

III.E. Methods for identifying biologic utility for a perturbation

In some embodiments, disclosed methods are used to identify a biological utility for a perturbation. These methods encompass measurements of any cellular-component (or combination of different cellular-components) that can be shown to be differentially present in cells having different states or phenotypes, e.g., diseased and normal phenotypes. That is, the presence, absence, or amount of cellular-component is associated with a cell state or phenotype. In an embodiment the method includes exposing a plurality of cells to a perturbation; carrying out a first differential cellular-component expression assay, the assay including accessing a first plurality of single-cell expression datasets obtained from a plurality of cells prior to and following exposure of the cells to the perturbation, each of the datasets including a vector of cellular-components $r_i$, each entry in the vector associated with one of a plurality of cellular-components, and the value of each entry representing a quantity of the cellular-component for the cell; applying a statistical technique to the first plurality of datasets to generate a set of differentially expressed cellular-components $E_k$ responsive to exposure to the perturbation; and determining a level of similarity between the set of differentially expressed cellular-components $E_k$ responsive to exposure to the perturbation, and a set of differentially expressed cellular-components $E_i$ associated with a difference between a diseased cell phenotype and a normal cell phenotype, wherein a significant level of similarity between $E_k$ and $E_i$ indicates a utility for the perturbation in transitioning cells between the diseased cell phenotype and the normal cell phenotype.

In some embodiments, applying the statistical technique includes performing dimensionality reduction (e.g., dimensionality reduction 320 of FIG. 3) on the first plurality of datasets 132 to generate a first matrix M, the first matrix M including rows in a first dimension and columns in a second dimension, the values of the matrix M including values generated from quantities of cellular-components located at that point in first and second dimension space; performing clustering to generate a first set of clusters $C_j$, each cluster including a plurality of points corresponding to a subset of the rows in first matrix M and their corresponding cell response states; and determining the set of differentially expressed cellular-components $E_k$ responsive to exposure to the perturbation for the cell using the first set of clusters $C_j$.

In some embodiments, the set of differentially expressed cellular-components $E_i$ associated with a difference between a diseased cell phenotype and a normal cell phenotype can be determined by carrying out a second differential cellular-component expression assay, the second assay including accessing a second plurality of single-cell cellular-component expression datasets obtained from a plurality of cells in different states, such as normal cells and diseased cells, each of the datasets including a vector of cellular-components $r_i$, each entry in the vector associated with one of a plurality of cellular-components, and the value of each entry representing a quantity of that cellular-component for that cell; and applying a statistical technique to the second plurality of datasets.

In some embodiments, applying a statistical technique to the second plurality of datasets includes performing dimensionality reduction on the second plurality of datasets to generate a second matrix M, the second matrix M including rows in a first dimension and columns in a second dimension, the values of the second matrix M including values generated from quantities of one or more of the cellular-components located at that point in first and second dimension space; performing manifold learning with the second matrix M with an approximation of the relative similarity of points to create a second matrix N including a plurality of rows and two columns, each row corresponding to one of the cells, each of the columns corresponding to one of two dimensions in a two-dimensional space, the values of the second matrix N indicating a relative difference in cell phenotype between each cell with respect to each other cell based on the datasets; performing clustering to generate a second set of clusters $C_j$, each cluster including a plurality of points corresponding to a subset of the rows in matrix N and their corresponding cell response states; and determining set of differentially expressed cellular-components $E_i$ associated with a difference between a diseased cell phenotype and a normal cell phenotype for the cell, indicating differences between the diseased cell phenotype and the normal cell phenotype, using the second set of clusters $C_j$.

In some embodiments, the perturbation is known to have an acceptable human safety profile determined by results obtained in a regulated clinical trial.

In some embodiments, the diseased cell phenotype is identified by a discrepancy between the diseased cell and a normal cell. For instance, in some embodiments, the diseased cell phenotype can be identified by loss of a function of the cell, gain of a function of the cell, progression of the cell (e.g., transition of the cell into a differentiated state), stasis of the cell (e.g., inability of the cell to transition into a differentiated state), intrusion of the cell (e.g., emergence of the cell in an abnormal location), disappearance of the cell (e.g., absence of the cell in a location where the cell is normally present), disorder of the cell (e.g., a structural, morphological, and/or spatial change within and/or around the cell), loss of network of the cell (e.g., a change in the cell that eliminates normal effects in progeny cells or cells downstream of the cell), a gain of network of the cell (e.g., a change in the cell that triggers new downstream effects in progeny cells of cells downstream of the cell), a surplus of the cell (e.g., an overabundance of the cell), a deficit of the cell (e.g., a density of the cell being below a critical threshold, a difference in cellular-component ratio and/or quantity in the cell, a difference in the rate of transitions in the cell, or any combination thereof.

In some embodiments, the diseased cells include cell lines, biopsy sample cells, and cultured primary cells. In some embodiments, the normal cells include cultured primary cells and biopsy sample cells. In some embodiments, the cells are human cells.

In some embodiments, the methods are used to select a perturbation useful for treating a disease, based on an indicated utility identified using the above-described methods. In some embodiments, the methods include treating a subject having a disease by administering to the subject an effective amount of a selected perturbation or a drug substance developed from a perturbation lead compound.

Embodiments

Embodiment 1. A method, including the steps of: accessing a plurality of single-cell cellular-component expression datasets, each dataset obtained from a cell of a plurality of cells that have transitioned away from a same "progenitor" cell type, each dataset including a vector of cellular-components $r_i$, each entry in the vector associated with one of a plurality of cellular-components, and the value of each entry representing a quantity of the cellular-component for the cell; performing dimensionality reduction on the datasets to generate a matrix M, the matrix M including rows in a first dimension and columns in a second dimension, each row corresponding to one cell of the plurality of cells, the values of the matrix M including values generated from quantities of cellular-components located at that point in first and second dimension space; performing clustering to generate a set of clusters $C_j$, each cluster including a plurality of points corresponding to a subset of the rows in matrix M and their corresponding cells; and determining a set of differentially expressed cellular-components $E_k$ for the cells using the set of clusters $C_j$.

Embodiment 2. The method of embodiment 1, further including performing manifold learning with the matrix M with an approximation of the relative similarity of points, to create a matrix N including a plurality of rows and two columns, each row corresponding to one of the plurality of cells, each of the columns corresponding to one of two-dimensions in a two dimensional space, the values of the matrix N indicating a relative cell type of each cell with respect to each other cell based on the datasets.

Embodiment 3. The method of any one of embodiments 1-2, wherein the cells are a heterogeneous population of cells having various cell types when the single-cell cellular-component expression datasets were obtained.

Embodiment 4. The method of any one of embodiments 1-2, wherein the cells are a substantially homogeneous population of cells having the "progenitor" cell type; and wherein the single-cell cellular-component expression datasets were obtained at each of a plurality of points in time as the cells transitioned away from the "progenitor" cell type, such that a different dataset of the plurality of datasets is collected for each cell and point-in-time combination.

Embodiment 5. The method of embodiment 4, wherein the plurality of time points includes at least three time points.

Embodiment 6. The method of any one of embodiments 4-5, wherein the plurality of time points includes a "progenitor" time point at which a substantial fraction of the cells have not yet transitioned away from the "progenitor" cell type.

Embodiment 7. The method of any one of embodiments 4-6, wherein the plurality of time points includes a transition time point at which a substantial fraction of the cells have transitioned away from the "progenitor" cell type.

Embodiment 8. The method of any one of embodiments 4-7, wherein the plurality of time points includes at least one intermediate time point at which a substantial fraction of the cells have at least partially transitioned away from the "progenitor" cell type.

Embodiment 9. The method of any one of embodiments 1-8, wherein the plurality of cellular-components are selected from the group consisting of nucleic acids, proteins, lipids, carbohydrates, nucleotides, and any combinations thereof.

Embodiment 10. The method of embodiment 9, wherein the nucleic acids are selected from the group consisting of DNA and RNA.

Embodiment 11. The method of embodiment 10, wherein the RNA is selected from the group consisting of coding and non-coding RNA.

Embodiment 12. The method of any one of embodiments 1-11, wherein the single-cell cellular-component expression datasets are generated using a method selected from the group consisting of: single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combinations thereof, as well as summaries of the same, including combinations, such as linear combinations, representing activated pathways in the single-cell cellular-component expression datasets.

Embodiment 13. The method of any one of embodiments 1-12, wherein performing dimensionality reduction includes performing principal component analysis (PCA) on the single-cell cellular-component expression datasets to generate the matrix M.

Embodiment 14. The method of any one of embodiments 1-13, wherein performing dimensionality reduction includes using a diffusion map on the single-cell cellular-component expression datasets to generate the matrix M.

Embodiment 15. The method of any one of embodiments 1-14, wherein performing dimensionality reduction includes using neural network autoencoders on the single-cell cellular-component expression datasets to generate the matrix M.

Embodiment 16. The method of embodiment 2, wherein performing manifold learning includes estimating a geometry of the data in matrix M to create the matrix N.

Embodiment 17. The method of embodiment 16, wherein performing manifold learning includes performing locally linear embedding.

Embodiment 18. The method of embodiment 16, wherein performing manifold learning includes performing local linear isometric mapping (ISOMAP).

Embodiment 19. The method of embodiment 16, wherein performing manifold learning includes performing t-distributed stochastic neighbor embedding (t-SNE).

Embodiment 20. The method of embodiment 16, wherein performing manifold learning includes performing Potential of Heat-Diffusion for Affinity Based Trajectory Embedding (PHATE).

Embodiment 21. The method of embodiment 16, wherein performing manifold learning includes performing Uniform Manifold Approximation and Projection (UMAP).

Embodiment 22. The method of embodiment 16, wherein performing manifold learning includes creating a force-directed layout.

Embodiment 23. The method of embodiment 22, wherein the force-directed layout is created using the Force Atlas 2 algorithm.

Embodiment 24. The method of any one of embodiments 1-23, wherein performing clustering assumes no prior knowledge of the organization of the plurality of points in each cluster.

Embodiment 25. The method of any one of embodiments 1-24, wherein performing clustering includes performing HDBSCAN to generate the set of clusters $C_j$.

Embodiment 26. The method of any one of embodiments 1-25, wherein performing clustering includes performing Louvain community detection to generate the set of clusters $C_j$.

Embodiment 27. The method of any one of embodiments 1-26, wherein performing clustering includes assigning each point to one of the clusters $C_j$ based on which point in time the single-cell cellular-component expression dataset associated with the point was collected.

Embodiment 28. The method of any one of embodiments 1-27, wherein performing clustering includes analyzing the plurality of points using a diffusion path algorithm that assigns a point to a cluster based on a measure of how terminal the point is from the cluster.

Embodiment 29. The method of any one of embodiments 1-28, wherein determining the set of differentially expressed cellular-components $E_k$ includes: for each cellular-component, for at least one of the clusters, comparing the quantity of the cellular-component for the plurality of points in the at least one cluster against the quantity of the cellular-component for the plurality of points in at least one other cluster; and responsive to the quantity of the cellular-component for the plurality of points in the at least one cluster being a threshold level greater than the quantity of the cellular-component for the plurality of points in the at least one other cluster, adding the cellular-component to the set of differentially expressed cellular-components $E_k$.

Embodiment 30. The method of embodiment 29, wherein the at least one cluster includes an on-lineage one of the clusters $C_j$, the on-lineage cluster containing a plurality of points identifiable as having a desired cell type.

Embodiment 31. The method of embodiment 30, wherein the at least one other cluster includes an off-lineage one of the clusters $C_j$, the off-lineage cluster containing points identifiable as having an undesired cell type.

Embodiment 32. The method of any one of embodiments 1-31, wherein determining the set of differentially expressed cellular-components $E_k$ includes: for each cellular-component, for at least one of the clusters, calculating a distance metric between the quantity of the cellular-component for the plurality of points in the at least one cluster and the quantity of the cellular-component for the plurality of points in at least one other cluster; and responsive to the distance metric being statistically significant, adding the cellular-component to the set of differentially expressed cellular-components $E_k$.

Embodiment 33. The method of any one of embodiments 1-32, further including screening the set of differentially expressed cellular-components $E_k$ against a transcription factor database to identify a set of differentially expressed transcription factors.

Embodiment 34. The method of embodiment 33, further including: performing empirical mode decomposition on the set of differentially expressed cellular-components $E_k$ to generate a pseudo-time representation of the datasets; and identifying the set of differentially expressed transcription factors based on the pseudo-time representation.

Embodiment 35. A method, including the steps of: accessing a plurality of single-cell cellular-component expression datasets, each dataset obtained from a cell of a plurality of cells that have transitioned away from a same "progenitor" cell type, each dataset including a vector of cellular-components $r_i$, each entry in the vector associated with one of a plurality of cellular-components, and the value of each entry representing a quantity of the cellular-component for the cell; generating a kNN graph using a kNN algorithm and using the single-cell cellular-component expression datasets; performing clustering to generate a set of clusters $C_j$, each cluster including a plurality of points, each point corresponding to a single-cell cellular-component expression dataset for a cell of the plurality of cells; and determining a set of differentially expressed cellular-components $E_k$ for the plurality of cells using the set of clusters $C_j$.

Embodiment 36. The method of embodiment 35, wherein determining the set of differentially expressed cellular-components $E_k$ includes determining a distance metric between the plurality of points in the clusters $C_j$.

Embodiment 37. A method, including the steps of: accessing a single-cell transition signature representing a measure of differential cellular-component expression between a first cell state and an altered cell state; accessing a perturbation signature representing a measure of differential cellular-component expression between unperturbed cells not exposed to a perturbation and perturbed cells exposed to the perturbation; and determining whether the perturbation is associated with the transition of cells between the first cell state and the altered cell state based on a comparison of the single-cell transition signature and the perturbation signature.

Embodiment 38. The method of embodiment 36, wherein accessing the single-cell transition signature includes: determining the single-cell transition signature based on a first plurality of single-cell cellular-component expression datasets, each first dataset obtained from a cell of a first plurality of cells in the first cell state, and on a second plurality of single-cell cellular-component expression datasets, each second dataset obtained from a cell of a second plurality of cells in an altered cell state.

Embodiment 39. The method of embodiment 38, wherein each dataset of the first and second pluralities of single-cell cellular-component expression datasets includes a vector of cellular-components $r_i$, each entry in the vector associated with one of a plurality of cellular-components, and the value of each entry representing a quantity of the cellular-component for the cell.

Embodiment 40. The method of any one of embodiments 38-39, further including: obtaining the first and second pluralities of single-cell cellular-component expression datasets, the obtaining including: performing dimensionality reduction on the first and second pluralities of single-cell cellular-component expression datasets to generate a matrix M, the matrix M including rows in a first dimension and columns in a second dimension, each row corresponding to one cell of the plurality of cells, the values of the matrix M including values generated from quantities of cellular-components located at that point in first and second dimension space; performing clustering to generate a set of clusters $C_j$, each cluster including a plurality of points corresponding to a subset of the rows in matrix M and their corresponding cells; identifying the first plurality of cells from a first cluster of the set of clusters $C_j$; identifying the second plurality of cells from a second cluster of the set of clusters $C_j$; obtaining the first plurality of single-cell cellular-component expression datasets from the first plurality of cells; and obtaining the second plurality of single-cell cellular-component expression datasets from the second plurality of cells.

Embodiment 41. The method of embodiment 40, further including performing manifold learning with the matrix M with an approximation of the relative similarity of points, to create a matrix N including a plurality of rows and two columns, each row corresponding to one cell of the first and second pluralities of cells, each of the columns corresponding to one of two dimensions in a two dimensional space, the values of the matrix N indicating a relative cell state of each cell with respect to each other cell based on the first and second pluralities of single-cell cellular-component expression datasets.

Embodiment 42. The method of any one of embodiments 40-41, wherein the steps are performed according to any one of the methods of embodiments 1-34.

Embodiment 43. The method of any one of embodiments 37-42, wherein accessing the perturbation signature includes: determining the perturbation signature based on a plurality of unperturbed single-cell cellular-component expression datasets of the unperturbed cells not exposed to the perturbation and on a plurality of perturbed single-cell cellular-component expression datasets of the perturbed cells exposed to the perturbation.

Embodiment 44. The method of any one of embodiments 37-43, wherein the unperturbed cells are control cells that have not been exposed to the perturbation of the perturbed cells, or wherein the unperturbed cells are an average over unrelated perturbed cells that have been exposed to the perturbation.

Embodiment 45. The method of any one of embodiments 37-44, further including the step of: filtering the single-cell transition signature and the perturbation signature to include cellular-components that are transcription factors.

Embodiment 46. The method of any one of embodiments 38-42, wherein determining the single-cell transition signature based on the first plurality of single-cell cellular-component expression datasets and the second plurality of single-cell cellular-component expression datasets includes: determining a difference in cellular-component quantities between the first and the second pluralities of single-cell cellular-component expression datasets using one of a difference of means test, a Wilcoxon rank-sum test (Mann Whitney U test), a t-test, a logistic regression, and a generalized linear model.

Embodiment 47. The method of embodiment 43, wherein determining the perturbation signature based on the unperturbed and the perturbed pluralities of single-cell cellular-component expression datasets includes: determining a difference in cellular-component quantities between the unperturbed and the perturbed pluralities of single-cell cellular-component expression datasets using one of a difference of means test, a Wilcoxon rank-sum test (Mann Whitney U test), a t-test, a logistic regression, and a generalized linear model.

Embodiment 48. The method of any one of embodiments 37-47, further including: filtering the single-cell transition signature and the perturbation signature to reduce a number of cellular-components included in the single-cell transition signature and the perturbation signature.

Embodiment 49. The method of embodiment 48, wherein filtering the single-cell transition signature and the perturbation signature includes reducing the number of cellular-components included in the single-cell transition signature and the perturbation signature according to a threshold p-value or according to a threshold number of cellular-components.

Embodiment 50. The method of any one of embodiments 37-49, wherein the perturbation signature includes a plurality of cellular-components, each cellular-component associated with a significance score quantifying an association between a change in quantity of the cellular-component and a change in cell state between the unperturbed cells and the perturbed cells, and wherein determining whether the perturbation is associated with the transition of cells between the first cell state and the altered cell state includes: replacing the significance score for each cellular-component with a matching score for the cellular-component; combining the matching scores for the plurality of cellular-components to generate a matching score for the perturbation; and determining whether the perturbation is associated with the transition of cells between the first cell state and the altered cell state based on the matching score for the perturbation.

Embodiment 51. The method of embodiment 50, wherein the matching scores include discrete or continuous scores.

Embodiment 52. The method of any one of embodiments 50-51, wherein replacing each significance score includes: replacing the significance score with a first score if the cellular-component quantity from the single-cell transition signature and the cellular-component quantity from the perturbation signature for that cellular-component are both up-regulated; replacing the significance score with a second score if the cellular-component quantity from the single-cell transition signature is up-regulated and the cellular-component quantity from the perturbation signature for that cellular-component is down-regulated; and replacing the significance score with a third score if the cellular-component quantity from the perturbation signature for that cellular-component is not significantly up-regulated or down-regulated.

Embodiment 53. The method of any one of embodiments 50-51, wherein replacing the significance score includes: replacing the significance score with a first score if the cellular-component quantity from the single-cell transition signature and the cellular-component quantity from the perturbation signature for that cellular-component are both down-regulated; replacing the significance score with a second score if the cellular-component quantity from the single-cell transition signature is down-regulated and the cellular-component quantity from the perturbation signature for that cellular-component is up-regulated; and replacing the significance score with a third score if the cellular-component quantity from the perturbation signature for that cellular-component is not significantly up-regulated or down-regulated.

Embodiment 54. The method of any one of embodiments 37-49, wherein the perturbation signature includes a plurality of cellular-components, each cellular-component associated with a significance score quantifying an association between a change in quantity of the cellular-component and a change in cell state between the unperturbed cells and the perturbed cells, and wherein determining whether the perturbation is associated with the transition of cells between the first cell state and the altered cell state includes: combining the significance scores for the plurality of cellular-components to generate a significance score for the perturbation; and determining whether the perturbation is associated with the transition of cells between the first cell state and the altered cell state based on the significance score for the perturbation.

Embodiment 55. The method of any one of embodiments 50-53, further including: estimating a false cellular-component discovery rate for the matching score for the perturbation by: calculating an empirical marginal expression frequency for each cellular-component of the plurality of cellular-components; summing the empirical marginal expression frequencies for the plurality of cellular-components over their combinations to generate a probability of identifying a number of cellular-components by chance assuming independently distributed expression; and estimating the false cellular-component discovery rate for the matching score for the perturbation based on the probability.

Embodiment 56. The method of embodiment 37-55, wherein determining whether the perturbation is associated with the transition of cells between the first cell state and the altered cell state includes: determining that a threshold quantity of covariates of the perturbation are associated with the transition of cells between the first cell state and the altered cell state; and responsive to the determination, determining that the perturbation is associated with the transition of cells between the first cell state and the altered cell state.

Embodiment 57. The method of embodiment 56, wherein the perturbation includes exposure of the cells to a small molecule, and wherein one or more covariates of the perturbation include: a specific dose of the small molecule, a time at which the differential cellular-component expression between the unperturbed and the perturbed cells is measured relative to a time at which the perturbed cells are exposed to the small molecule, and a cell line of the perturbed cells.

Embodiment 58. The method of any one of embodiments 37-57, wherein cellular-components include genes.

Embodiment 59. The method of embodiment 37-58, wherein the single-cell cellular-component expression datasets are generated using a method selected from the group consisting of: single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combinations or summaries thereof.

Embodiment 60. The method of embodiment 37-59, wherein at least one of the single-cell transition signature and the perturbation signature is obtained from a database.

Embodiment 61. The method of embodiment 60, wherein the perturbation signature is obtained from a database including a plurality of perturbation signatures for a plurality of perturbations, and wherein the method further includes: for each perturbation of the plurality of perturbations in the database: accessing the perturbation signature for the perturbation from the database; and determining whether the perturbation is associated with the transition of cells between the first cell state and the altered cell state based on a comparison of the single-cell transition signature and the perturbation signature.

Embodiment 62. The method of any one of embodiments 37-61, further including accessing a plurality of perturbation signatures for a plurality of perturbed cells; and for each of the plurality of perturbation signatures, carrying out the determining step, thereby screening for perturbations that promote the altered cell state.

Embodiment 63 The method of embodiment 62, wherein accessing the plurality of perturbation signatures includes exposing cells to a plurality of perturbations to generate the plurality of perturbed cells; and measuring a plurality of cellular-component quantities from the plurality of perturbed cells.

Embodiment 64. The method of any one of embodiments 37-63, further including identifying a perturbation that promotes the altered cell state.

Embodiment 65. The method of embodiment 64, wherein promoting the altered cell state includes, in a population of cells including the first cell state, promoting a transition from the first cell state to the altered cell state.

Embodiment 66. The method of embodiment 64, wherein promoting the altered cell state includes, in a population of cells including the first cell state, increasing a ratio of the number of cells in the alternate state to the number of cells in the first state, or, optionally, in a state other than the altered cell state.

Embodiment 67. The method of embodiment 64, wherein promoting the altered cell state includes, in a population of cells including the first cell state, increasing an absolute number of cells in the altered cell state.

Embodiment 68. The method of embodiment 64, wherein promoting the altered cell state includes, in a population of cells including the first cell state, decreasing an absolute number of cells in the first cell state or, optionally, in a state other than the altered cell state.

Embodiment 69. The method of any one of embodiments 37-68, wherein the cell transition signature and the perturbation signature are generated using different types of cellular-components.

Embodiment 70. The method of any one of embodiments 37-68, wherein the cell transition signature and the perturbation signature are generated using the same types of cellular-components.

Embodiment 71. A method, including the steps of: accessing a single-cell transition signature representing a measure of differential cellular-component expression between a first cell state and an altered cell state; accessing a plurality of perturbation signatures, each perturbation signature associated with a perturbation and representing a measure of differential cellular-component expression between unperturbed cells not exposed to the perturbation and perturbed cells exposed to the perturbation; and determining a subset of the perturbations that are associated with the transition of cells between the first cell state and the altered cell state based on a comparison of the single-cell transition signature and the plurality of perturbation signatures.

Embodiment 72. The method of embodiment 71, wherein each perturbation signature includes a plurality of cellular-components, each cellular-component associated with a significance score quantifying an association between a change in quantity of the cellular-component and a change in cell state between the unperturbed cells and the perturbed cells, and wherein determining a subset of the perturbations that are associated with the transition of cells between the first cell state and the altered cell state includes: for each perturbation signature: replacing the significance score for each cellular-component with a matching score for the cellular-component; and combining the matching scores for the plurality of cellular-components to generate a matching score for the perturbation; ranking the perturbations according to their matching scores; and selecting the subset of the perturbations based on the ranked list of perturbations.

Embodiment 73. A computer program product including a non-transitory computer readable storage medium having instructions encoded thereon that, when executed by a processor, cause the processor to execute the method of any one of embodiments 37-72.

Embodiment 74. A system including: a non-transitory computer readable storage medium having instructions encoded thereon that, when executed by a processor, cause the processor to execute the method of any one of embodiments 37-72.

Embodiment 75. A method for promoting neurons and/or progenitor cells, including: exposing a starting population of cells including fibroblasts to a perturbation having a perturbation signature that promotes the transition of the starting population of cells including fibroblasts into progenitor cells and/or neurons, wherein the perturbation signature is increased activity of one or more of Brn2, Ascl1, Myt1, Zfp941, Taf5B, St18, Zkscan16, Camta1, and Arnt2, and/or decreased activity of one or more of Ascl1, Atf3, Rorc, Scx, Satb1, Elf3, and Fos.

Embodiment 76. The method of embodiment 75, wherein the neurons and/or progenitor cells are promoted by one or more of: increasing the absolute number of neurons and/or progenitor cells, decreasing the absolute number of fibroblasts, promoting transition of fibroblasts into neurons and/or progenitor cells, promoting the lifespan of neurons or progenitor cells, decreasing the lifespan of fibroblasts, or increasing the ratio of neurons and/or progenitor cells to fibroblasts.

Embodiment 77. The method of embodiment 75, wherein the perturbation does not include Forskolin, PP1, PP2, and Trichostatin A.

Embodiment 78. A method of increasing a quantity of neurons and/or progenitor cells, including exposing a population of cells including fibroblasts to a pharmaceutical composition, the pharmaceutical composition having a perturbation signature that promotes the transition of the population of cells including fibroblasts into neurons, wherein the pharmaceutical composition includes Forskolin, PP1, PP2, Trichostatin A, BRD-K38615104, Geldanamycin, Manumycin A, Mitoxantrone, Curcumin, Alvocidib, Varinostat, KI20227, or a combination of the foregoing, e.g., 2, 3, 4, 5, or more of the foregoing.

Embodiment 79. The method of embodiment 78, wherein the pharmaceutical composition does not include Forskolin, PP1, PP2, and Trichostatin A.

Embodiment 80. A pharmaceutical composition for promoting neurons and/or progenitor cells, including: a perturbation selected from the group consisting of Forskolin, PP1, PP2, Trichostatin A, BRD-K38615104, Geldanamycin, Manumycin A, Mitoxantrone, Curcumin, Alvocidib, Varinostat, KI20227, or a combination of the foregoing, and a pharmaceutically-acceptable excipient.

Embodiment 81. The pharmaceutical composition of embodiment 80, wherein the perturbation does not include Forskolin, PP1, PP2, and Trichostatin A.

Embodiment 82. A unit dosage form including a pharmaceutical composition of embodiment 80 or 81.

Embodiment 83. A method of identifying a candidate perturbation for promoting the transition of a starting population of cells including fibroblasts into neurons and/or progenitor cells, the method including: exposing the starting population of cells including fibroblasts to a perturbation; identifying a perturbation signature for the perturbation, the perturbation signature including one or more cellular-components and a significance score associated with each cellular-component, the significance score of each cellular-component quantifying am association between a change in expression of the cellular-component and a change in cell state of the population of cells from fibroblasts to neurons and/or progenitor cells following exposure of the population of cells to the perturbation; and identifying the perturbation as a candidate perturbation for promoting the transition of a population of cells including fibroblasts into neurons and/or progenitor cells based on the perturbation signature, wherein the perturbation signature is increased activity of one or more of Brn2, Ascl1, Myt1, Zfp941, Taf5B, St18, Zkscan16, Camta1, and Arnt2, and/or decreased activity of one or more of Ascl1, Atf3, Rorc, Scx, Satb1, Elf3, and Fos.

IV. Example 0, 1, 2, and 3—Identifying Causality and Controlling Cell Fate in Mouse Embryonic Fibroblasts Differentiating into Neurons and Myocytes The following examples validate the methods introduced in Sections II and III above. In more detail, the examples demonstrate the ability of the methods of Sections II and III to accurately identify genes and/or perturbations that are known to impact the trajectory of cell state transition. Further, the examples discussed below demonstrate the ability of the methods of Section II and III to generate novel biological insights that can be used to control the trajectory of cell state transition. Specifically, the examples demonstrate the ability of the methods of Sections II and III to identify factors (e.g., genes and perturbations) that impact cell state transition that are not previously known.

The examples discussed below applied the methods of Sections II and III to a combination of publicly available data and in vitro experimental data to validate several known and previously unknown factors (e.g., genes and perturbations) that impact the trajectory of cell state transition. The results of this application of the methods of Sections II and III to the combination of publicly available data and in vitro experimental data are shown in FIGS. 4B-5A and 7A-9.

Figure 6:
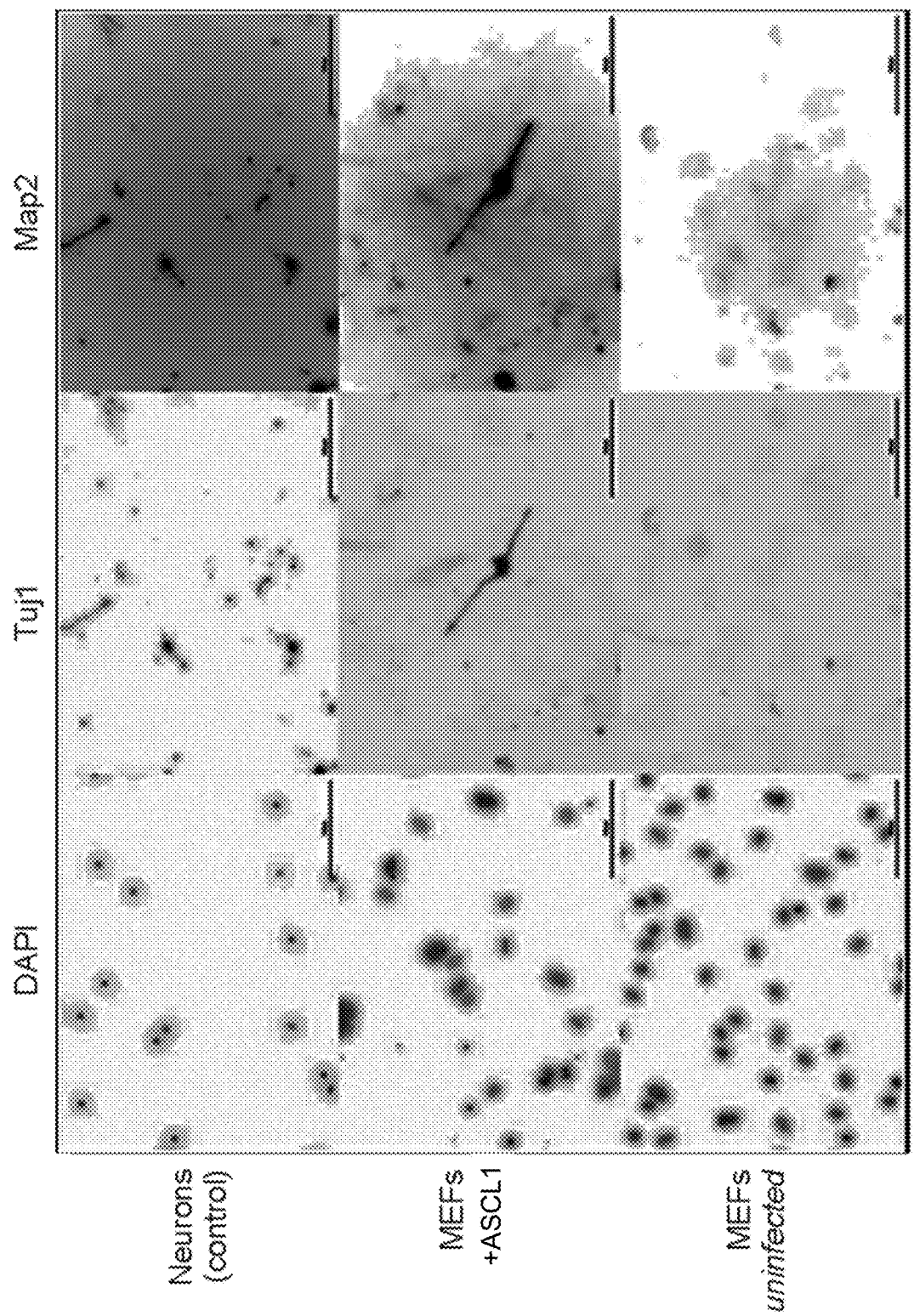
FIG. 6 depicts images of MEF cells, in which expression of the Ascl1 transcription factor is forced, that have been stained with DAPI, Map2 antibodies, and Tuj1 antibodies, images of mouse neurons stained with DAPI, Map2 antibodies, and Tuj1 antibodies, and images of MEF cells in which expression of the Ascl1 transcription factor is not forced that have been stained with DAPI, Map2 antibodies, and Tuj1 antibodies, in accordance with an embodiment of the present disclosure.

Some of these results were also validated using only the in vitro experimental data. The results of this in vitro validation are shown in FIG. 6. The in vitro experimental data was obtained by growing and measuring cells according to the protocol discussed in Section IV.A below.

IV.A. Example 0: In Vitro Cell Handling and Dataset Gathering

This section describes the protocol for the in vitro experiment mentioned above. The data from this in vitro experiment was pooled with publicly available data to generate FIGS. 4B-5A and 7A-9, and was used independently to generate FIG. 6.

This section applies the generalized protocol described in Section II to the specific example of evaluating mouse embryonic fibroblasts (MEFs) differentiating into neurons or myocytes. In this particular example, neurons were the on-lineage cell, myocytes were the off-lineage cell, and MEFs were the "progenitor" cell. The protocol also included additional steps including lentiviral overexpression of the gene Ascl1 and perturbation mediation.

The MEF media was 10% Fetal Bovine Serum (FBS) in Dulbecco's Modified Eagle Medium (DMEM), 1× Glutamax, 1× Non-essential amino acids, Pen/strep, and beta-Mercaptoethanol. The neuronal media was DMEM/F12, N2, B27, 1× Glutamax, and Insulin 25 µg/ml.

The protocol that was followed is listed below:
Day 0: Thaw 1 million MEF cells into a 10 cm plate in a MEF media.
Day 1: Seed at 20K/well into a 24 well plate.
    If applicable, simultaneously spin infect with Ascl1 virus (Multiplicity of infection (MOI) 8). Spin at 2000 rpm for 1 hour at 32° C. in the presence of a MEF media (250 µl/well) and polybrene 8 µg/ml.
    Perform single-cell ribonucleic acid (RNA) sequencing (scRNA-seq) to obtain d2 dataset for each cell.
Day 2: Change media to wash out polybrene (MEF media) for viral experiment.
    For perturbation experiment, add small molecules (resuspended in dimethyl sulfoxide (DMSO) or Ethanol).
Day 3: Change media to neuronal media.
    For perturbation experiment, add molecules (resuspended in DMSO or Ethanol).
Day 5: Half-media change (add small molecules if applicable)
Day 8: Half-media change (add small molecules if applicable)
Day 9: Half-media change (add small molecules if applicable)
Day 11: Half-media change (add small molecules if applicable)
Day 13: Half-media change (add small molecules if applicable)
Day 15: Fix plate and stain with Map2 and Tuj1 antibodies. Image on Molecular Devices HCl IXM4 or other high content imaging microscope by scanning each well. Quantify number of Map2/Tuj1 positive neurons per well.

IV.B. Example 1, 2, and 3: In Vitro Cell Handling and Dataset Gathering

Figure 4A:
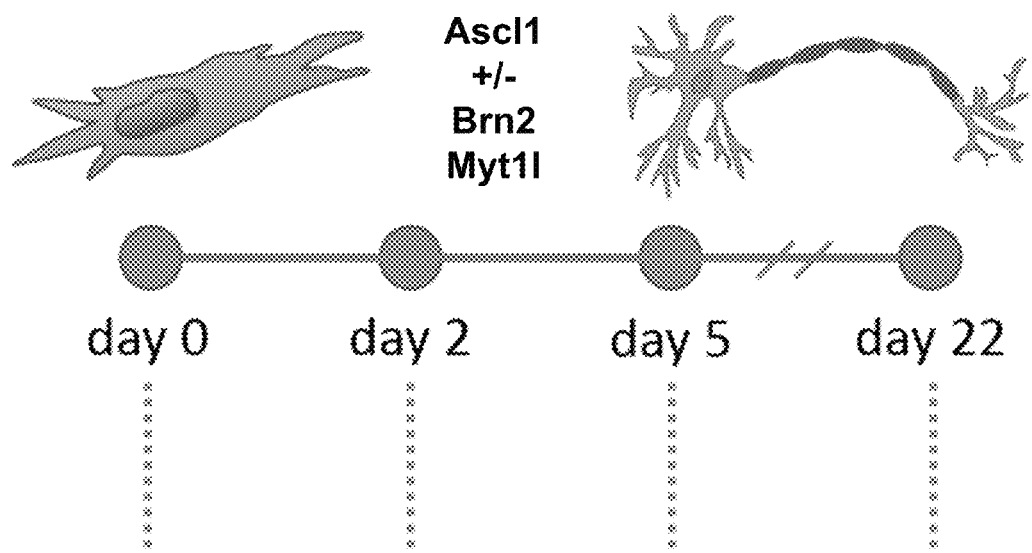
FIG. 4A depicts a timeline that tracks the trajectory of induced cell state transition over a period of time, in accordance with an embodiment of the present disclosure.
Figure 4B:
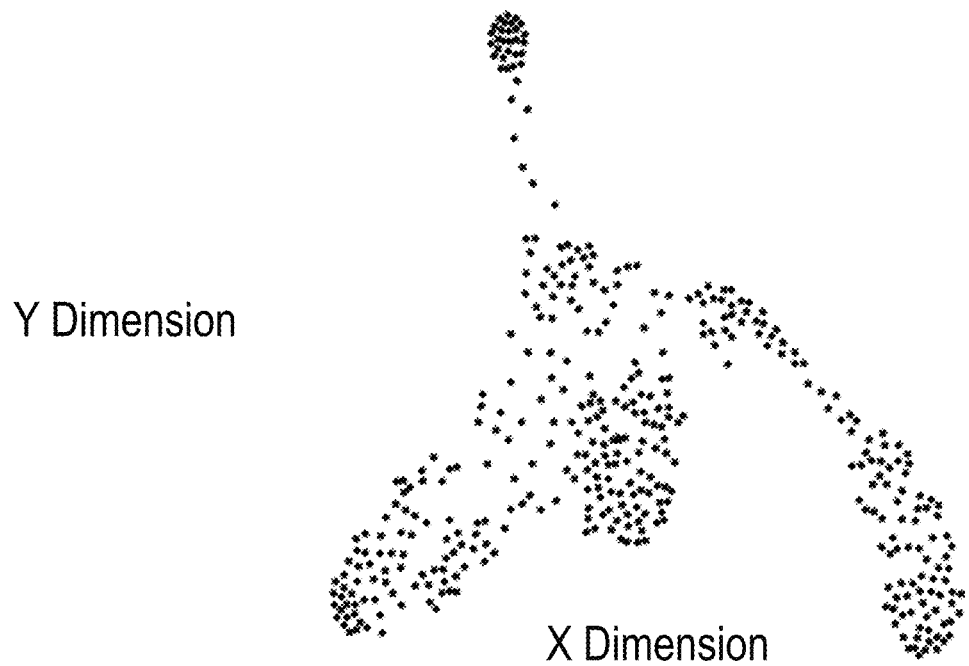
FIG. 4B depicts a manifold generated by a force-directed layout algorithm for the example matrix N in Supplementary Table 1, in accordance with an embodiment of the present disclosure.

FIG. 4A depicts a timeline that tracks the trajectory of induced cell state transition over a period of time, in accordance with an embodiment. More specifically, FIG. 4A depicts a timeline that tracks the trajectory of induced transition of MEFs over a 23 day period of time—from day 0 to day 22.

As shown in FIG. 4A, at day 0 of the 23 day time period, MEFs were obtained. In alternative embodiments, the trajectory of transition of any single-cell can be studied according to similar methods. For example, in alternative examples, the trajectory of transition of mouse embryonic hemocytoblasts may be studied according to similar methods.

At day 0 of the 23 day period of time, each MEF of the population MEFs was transduced with the appropriate transcription factor(s). As shown in FIG. 4A, only Ascl1 or Brn2, Ascl1, and Myt1 (known collectively as the BAM transcription factors) was overexpressed in the MEFs. Specifically, in the in vitro experiment that used the protocol of Section IV.A above to generate FIG. 6, only Ascl1 was overexpressed in the MEFs. Conversely, to generate the publicly available data to which the methods of Sections II and III were applied to generate FIGS. 4B-5A and 7A-9, each of Brn2, Ascl1, and Mytl1 was overexpressed in the MEFs.

In the embodiment disclosed herein, expression of the Ascl1 transcription factor was forced by inducible expression of Ascl1 following lentiviral delivery. In alternative embodiments, expression of one or more transcription factors may be forced by any alternative means. For example, in alternative embodiments, expression of one or more transcription factors may be forced by transposons, mRNA delivery, or another type of viral delivery.

Forced expression of one or more of the BAM transcription factors is known to cause one or more of the forced MEFs to more commonly transition into mouse "progenitor" cells, mouse neurons, and/or mouse myocytes. Specifically, as is known in the literature, Ascl1 priming induces MEFs to transition into mouse "progenitor" cells, expression of Ascl1 alone induces the mouse "progenitor" cells to transition into mouse neurons and mouse myocytes, and expression of Brn2 and Mytl1 induces the mouse "progenitor" cells to transition into mouse neurons. However, this induction of cell state transition by the one or more of the BAM transcription factors does not occur with 100% efficiency. Specifically, as is known in the literature, the BAM transcription factors induce transition of MEFs into mouse neurons with 20% efficiency. In other words, despite expression of one or more of the BAM transcription factors, some cells may fail to transition as expected. In some embodiments, this failed transition is known as failed reprogramming.

The mouse cells in which the one or more of the BAM transcription factors were forcibly expressed were monitored over the 23 day time period. More specifically, for the mouse cells in which expression of Ascl1 was forced, single-cell RNA-sequencing (scRNA-seq) measurements for each single mouse cell of the mouse cells in the population were obtained on days 2, 5, and 22 during the 23 day period of time. Alternatively, for the mouse cells in which expression of all of the BAM factors was forced, scRNA-seq measurements for each single mouse cell of the mouse cells in the population were obtained only on day 22 during the 23 day period of time.

In alternative embodiments, RNA-sequencing measurements can be taken at any number of time points at any frequency. More specifically, to accurately capture cell state transition trajectories, the time points at which RNA-sequencing measurements are taken ideally generally correspond to the time points at which one or more transition trajectories diverge. An RNA-sequencing measurement for a single-cell on a particular day includes quantification of mRNA expression in the single-cell on that particular day. In other words, an RNA-sequencing measurement for a single-cell on a particular day includes a count of each mRNA transcript in the single-cell on that particular day. Furthermore, because each mRNA transcript is associated with a specific gene, an RNA-sequencing measurement for a single-cell on a particular day includes quantification of gene expression in the single-cell on that particular day. However, in practice, the cells will often not be entirely homogeneous in their state of cell state transition, and so measurement of cell state transition on a given day is predicted to capture a distribution of cells at various stages of cell state transition.

The in vitro protocol in which Ascl1 was overexpressed in the MEFs was used to perform the validation experiment depicted in FIG. 6 and described in detail below. Additionally, the gene expression measurements obtained from the in vitro protocol in which Ascl1 was overexpressed in the MEFs were pooled with the publicly available gene expression measurements from the MEFs in which all of the BAM factors were overexpressed. This pool of in vitro and publicly available data was then used to generate the data depicted in FIGS. 4B-5A and 7A-9. As noted above, these figures serve to both validate the ability of the methods of Sections II and III to accurately identify genes that influence cell state transition, but also demonstrate the ability of the methods described in Section II and III to generate novel biological insights that are useful in controlling the trajectory of cell state transition and thus cell fate.

IV.C. Example 1: Dimensionality Reduction Validating Literature Identified Transition As discussed above, gene expression measurements obtained on days 2, 5, and 22 from MEFs in which only Ascl1 was overexpressed were pooled with the publicly available gene expression measurements taken on day 22 from MEFs in which all of the BAM factors were overexpressed. Using the methods described above in Section II, for each of the days on which gene expression in the cells was measured, the gene expression measurements for each of the cells were used to generate a dataset of a vector of transcripts $r_i$. Each vector of transcripts $r_i$ was associated with a particular cell on a particular day on which the gene expression measurements contained in the vector of transcripts $r_i$ were obtained. Each transcript in the vector of transcripts $r_i$ was associated with a particular gene in the genome of the cell, and the value of each entry in the vector of transcripts $r_i$ represented a sequencing depth (transcript count) of the transcript on the particular day that was associated with the vector of transcripts $r_i$.

As discussed above with regard to Section III.C., dimensionality reduction was performed on the datasets that encoded the gene expression measurements for each of the cells on each of the measurement days. In this example, principle component analysis (PCA) was used to perform the dimensionality reduction and to produce a dimensionally-reduced matrix M.

Next, manifold learning was performed on the matrix M to generate a further dimensionally-reduced matrix N. In this example, a force-directed layout algorithm was used to generate the matrix N. Matrix N is depicted in Supplementary Table 1. Matrix N is also plotted as a force-directed layout manifold depicted in FIG. 4B. The plotted data in the manifold of FIG. 4B corresponds to the matrix N data in Supplementary Table 1. Note that the matrix N was used primarily for visualization purposes and need not be generated in some embodiments. In other words, in some embodiments, manifold learning is not performed on the matrix M.

As discussed above, each point in the manifold is associated with one of the rows of the matrix N, which is associated with a particular cell of the cells on a particular day of the four days on which gene expression was measured for the cell. Furthermore, each point is associated with a dataset of gene transcript counts measured for the particular cell on the particular day. In interpreting the manifold of FIG. 4B, because the values of the dimension x and the dimension y in a row of the manifold are based on the gene transcript counts for the cell on the day associated with that row, the positioning of a point in the manifold reflects the gene transcript counts for the cell on the day associated with the point, relative to the other points, and thus the other cells on the other days, in the manifold. As a result, visualizing the manifold allows observation of the shifting gene transcript counts of various genes for the cells over the 23 day period of time.

In the manifold depicted in FIG. 4B, all points are represented by identical shapes with identical coloring. Therefore, in the manifold of FIG. 4B, the only discernable information provided by a point is its position (x,y) in the manifold. However, the gene-by-gene transcript counts and the particular day on which the gene transcript counts were obtained for each point are not discernable in FIG. 4B. As discussed in further detail below, the shapes of the points in the manifold of FIG. 5A are varied to indicate, in part, the day on which the gene transcript counts were obtained for each point, and thus each cell. Similarly, the shading of the points in the manifolds of FIG. 5B is varied to indicate the gene transcript counts on a gene-by-gene basis for each point, and thus for each cell on each measurement day.

FIG. 5A depicts the manifold of FIG. 4B, in accordance with an embodiment. In the embodiment of the manifold depicted in FIG. 5A, each point in the manifold is labeled with the day on which transcription factor expression for the cell associated with the point was measured, and with a qualitative stage at which the cell was in the transition process. For example, a point labeled with square shape in the manifold in FIG. 5A indicates that the point is associated with a cell on day 5 that was qualitatively characterized as an early induced neuronal (iN) cell.

By labeling each of the points in the manifold with a day on which gene expression for the cell associated with the point was measured and with a qualitative stage of the cell's transition, trajectories of transition can be identified. For example, two distinct trajectories of transition are indicated by arrows underlying the manifold in FIG. 5A. One identified trajectory delineates the trajectory of transition of a MEF cell to a mouse neuron. Another identified trajectory in FIG. 5A delineates the trajectory of transition of a MEF cell to a mouse myocyte.

By identifying the differences in gene expression between points (e.g., cells) at different stages along a trajectory of transition, the genes that contribute to the transition of a cell along a particular trajectory can be identified. But perhaps more importantly, by identifying the differences in gene expression between points (e.g., cells) at a juncture at which two or more trajectories of transition diverge, the genes that contribute to this divergence in transition trajectory can be identified. These identified genes can then be predicted to be associated with a particular trajectory and/or stage of transition. For example, if an increased level of expression of a gene A is identified in the cells labeled as day 5 early iN cells relative to the cells labeled as day 5 early myocytes, it may be hypothesized that expression of the gene A is associated with the trajectory of transition from MEFs to mouse neurons, as opposed to the trajectory of transition from MEFs to mouse myocytes.

As discussed above, FIG. 5A establishes the trajectories of transition based both on quantitative time points during the cells' transition processes, and on qualitative stages of the cells' transition processes. However, FIG. 5A does not indicate levels of gene expression on a gene-by-gene basis for the points (e.g., cells at different time points). Therefore, based on the information depicted in FIG. 5A, it is not possible to predict which genes are associated with which trajectories of transition. However, as noted above, the shading of the points in the manifolds of FIG. 5B is varied to indicate the relative gene transcript counts on a gene-by-gene basis for each point. Based on this depiction of gene expression for the points (e.g., cells at different time points) on a gene-by-gene basis, predictions of which genes are associated with which trajectories of transition can be made.

FIG. 5B depicts the level of expression of each of the three BAM transcription factors in each of the cells on each of the measurement days (days 2, 5, and 22 for Ascl1 and day 22 for Brn2 and Mytl1) depicted as points in the manifold of FIG. 4B, in accordance with an embodiment. Specifically, FIG. 5B depicts three distinct versions of the manifold of FIG. 4B. A first version of the manifold depicted in FIG. 5B depicts the level of expression of the Ascl1 transcription factor for each of the points of the manifold, a second version of the manifold depicted in FIG. 5B depicts the level of expression of the Brn2 transcription factor for each of the points of the manifold, and a third version of the manifold depicted in FIG. 5B depicts the level of expression of the Mytl1 transcription factor for each of the points of the manifold.

In FIG. 5B, the level of expression of a transcription factor for a point (e.g., a cell at a time point) in the manifold is measured as the log of fragments per kilobase of transcript per million mapped reads (FPKM) for the transcription factor. A relatively lower value of log(FPKM) indicates a relatively lower level of transcription factor expression. On the other hand, a relatively higher value of log(FPKM) indicates a relatively higher level of transcription factor expression. In the manifolds of FIG. 5B, a relatively lower level of expression of a transcription factor (e.g., a relatively lower value of log(FPKM)) for a point is indicated by shading the point relatively darker. Contrastingly, a relatively higher level of expression of a transcription factor (e.g., a relatively higher value of log(FPKM)) for a point is indicated by shading the point relatively lighter.

By comparing the trajectories of transition delineated in FIG. 5A with the manifolds of FIG. 5B that depict expression level of the BAM transcription factors on a gene-by-gene basis, the transcription factors that influence the progression of cells along a particular transition trajectory were identified.

Turning first to the manifold of FIG. 5B that depicts expression of the Ascl1 transcription factor, on day 0 during the 23 day time period, the mouse cells were just transduced with Ascl1 or with BAM. Therefore, the day 0 cells did not express Ascl1 at detectable levels. These day 0 cells that did not express Ascl1 were MEFs. Then, on day 2 of the 23 day time period, Ascl1 was expressed at a relatively low level as depicted by the relatively dark shading of the points associated with the day 2 cells. These day 2 cells that expressed Ascl1 began to progress along the trajectories of transition shown in FIG. 5A. Specifically, some of the day 2 cells became progenitor mouse cells, some of the day 2 cells became intermediate cells on the transition trajectory from MEFs to neurons, and some of the day 2 cells became induced cells on the transition trajectory from MEFs to myocytes. Similarly, on day 5 of the 23 day time period, expression of Ascl1 in the day 5 cells was increased relative to the day 2 cells, as depicted by the relatively lighter shading of the points associated with the day 5 cells. These day 5 cells that had increased expression of Ascl1 progressed further along the trajectories of transition shown in FIG. 5A. Specifically, the day 5 cells on the transition trajectory from MEFs to neurons became intermediate and early iN cells, while the day 5 cells on the transition trajectory from MEFs to myocytes became early myocytes. Finally, on day 22 of the 23 day time period, expression of Ascl1 in the day 22 cells increased or remained the same relative to the day 5 cells. These day 22 cells that expressed Ascl1 progressed further along the trajectories of transition shown in FIG. 5A. Specifically, the day 22 cells on the transition trajectory from MEFs to neurons became full-fledged mouse neurons, while the day 22 cells on the transition trajectory from MEFs to myocytes became full-fledged mouse myocytes. There were no mouse progenitor cells remaining on day 22.

These observations of MEF cell state transition following induction of Ascl1 expression adhere to trends that are known in the literature. Specifically, as briefly discussed above, Ascl1 priming induces MEFs to transition into mouse progenitor cells and expression of Ascii alone induces the mouse progenitor cells to transition into mouse neurons and mouse myocytes. As discussed above with regard to the Ascl1 manifold of FIG. 5B, following the forced expression of Ascl1 in the MEFs on day 0, the MEFs transitioned into any one of mouse progenitor cells, mouse myocytes, and mouse neurons.

Turning next to the manifold of FIG. 5B that depicts expression of the Brn2 transcription factor, on day 0 during the 23 day time period, the MEFs were transduced with the BAM factors. Brn2 expression was only measured on day 22 during the 23 day time period. As seen in FIG. 5B, on day 22 of the 23 day time period, the day 22 mouse neurons strongly expressed Brn2. Therefore, it can be deduced that expression of Brn2 is associated with progression of the MEF cells along the transition trajectory from MEFs to mouse neurons.

This observation of MEF cell state transition following induction of Brn2 expression adheres to a trend that is known in the literature. Specifically, as briefly discussed above, Brn2 expression induces mouse progenitor cells to transition into mouse neurons. As discussed above with regard to the Brn2 manifold of FIG. 5B, the MEFs that expressed Brn2 transitioned into mouse neurons.

Turning finally to the manifold of FIG. 5B that depicts expression of the Mytl1 transcription factor, on day 0 during the 23 day time period, the MEFs were transduced with the BAM factors. Mytl1 expression was only measured on day 22 during the 23 day time period. On day 22 of the 23 day time period, the day 22 mouse neurons strongly expressed Mytl1. Therefore, similar to the Brn2 transcription factor, it can be deduced that expression of Mytl1 is associated with progression of the MEF cells along the transition trajectory from MEFs to mouse neurons.

This observation of MEF cell state transition following induction of Mytl1 expression adheres to the trend that is known in the literature. Specifically, as briefly discussed above, Mytl1 expression induces mouse progenitor cells to transition into mouse neurons. As discussed above with regard to the Mytl1 manifold of FIG. 5B, the MEFs that expressed Mytl1 transitioned into mouse neurons.

Therefore, these observations attained by generating the Ascl1, Brn2, Mytl1 manifolds in FIG. 5B using the methods of Sections II and III are consistent with observations that are documented in the literature. This consistency of observations of Ascl1-aided, Brn2-aided, Mytl1-aided transition helps to validate the ability of the methods of Sections II and III to accurately identify genes that influence cell state transition.

To further validate the ability of the methods of Sections II and III to accurately identify genes that influence cell state transition, an in vitro experiment was performed to confirm the above observations made based on the manifolds of FIGS. 5A and 5B. Specifically, an in vitro experiment was performed to confirm the above observations that Ascl1 expression induces MEFs to transition into mouse "progenitor" cells, mouse neurons, and/or mouse myocytes.

The in vitro experiment was performed according to the protocol laid out above in Section IV.A. As discussed above, in this protocol, expression of Ascl1 alone was forced in the MEFs. Following the forced expression of the Ascl1 transcription factor in the MEFs on day 0 of the 23 day period, on day 15 of the 23 day period, the mouse cells were stained with DAPI, Map2 antibodies, and Tuj1 antibodies. DAPI is known to stain adenine-thymine rich regions in DNA. Thus DAPI stains cell nuclei. Map2 antibodies and Tuj1 antibodies are known to stain neural cells. Therefore, by staining the mouse cells with DAPI, Map2 antibodies, and Tuj1 antibodies, the quantity of mouse neurons relative to the quantity of overall mouse cells can be identified, and therefore the impact of Ascl1 over expression on transition of MEFs can be determined. This set of mouse cells in which expression of Ascl1 transcription factor was forced is referred to herein as the experimental group in the in vitro experiment.

As a positive control group in the in vitro experiment, a sample of mouse cells solely including mouse neurons, was also stained with DAPI, Map2 antibodies, and Tuj1 antibodies. As a negative control group, a sample of MEF cells in which Ascl1 expression was not forced was also stained with DAPI, Map2 antibodies, and Tuj1 antibodies.

Following staining of the experimental group, the positive control group, and the negative control group with DAPI, Map2 antibodies, and Tuj1 antibodies, each group stained with each stain was imaged on Molecular Devices HCl IXM4. The resulting images are shown in FIG. 6. FIG. 6 depicts images of MEF cells in which expression of Ascl1 is forced that have been stained with DAPI, Map2 antibodies, and Tuj1 antibodies, images of mouse neurons stained with DAPI, Map2 antibodies, and Tuj1 antibodies, and images of MEF cells in which expression of Ascl1 is not forced that have been stained with DAPI, Map2 antibodies, and Tuj1 antibodies, in accordance with an embodiment.

Turning first to the images of the negative control group, as shown in FIG. 6, the nuclei of the DAPI-stained MEF cells in which expression of Ascl1 was not forced are visible, but there are few to no neurons in the images depicting Map2 and Tuj1 staining of the MEF cells in which expression of Ascl1 was not forced. In other words, while there were many mouse cells (specifically MEFs) present in the sample, there were no neurons present. This is an expected result because expression of Ascl1 was not forced in the MEF cells of this sample, and therefore the transition of the MEF cells to neurons was not induced.

Turning next to the images of the positive control group, as shown in FIG. 6, the nuclei of the DAPI-stained mouse neurons are visible, and these same mouse neurons are also visible in the images depicting Map2 and Tuj1 staining of the mouse neurons. In other words, all of the cells in the positive control sample were accurately identified as neurons.

Turning finally to the images of the experimental group, as shown in FIG. 6, the nuclei of the DAPI-stained MEF cells in which expression of Ascl1 was forced are visible. Furthermore, some of these DAPI-stained cells were also stained with Map2 and Tuj1, indicating that these select cells were mouse neurons. Therefore, it can be inferred that forced expression of Ascl1 is associated with induction of transition from a MEF to a mouse neuron.

The in vitro experiment of FIG. 6 confirms that forced expression of Ascl1 in MEF cells can result in transition of the MEF cells to mouse neurons, as observed in the in silico experiments described above with regard to FIGS. 5A and 5B. This confirmation of the observations made in FIGS. 5A and 5B further validates the ability of the methods of Sections II and III. to accurately identify genes that influence cell state transition.

IV.D. Example 2: Clustering

As discussed above in Section III.C., following generation of a matrix M by dimensionality reduction, clustering is performed to group the data in the matrix M to generate a set of clusters $C_j$. Each cluster in the set of clusters $C_j$ includes a set of points.

FIG. 7A depicts the manifold of FIG. 4B, with the points in the manifold grouped into clusters $C_j$ identified by clustering, in accordance with an embodiment. In the embodiment of FIG. 7A, the clustering was performed using Louvain community detection, specifically GenLouvain Community Detection. As seen in FIG. 7A, the clustering identified 10 unique clusters $C_j$ of points in the manifold.

In general, clustering assigns points in a manifold to a given cluster based on a threshold similarity of the values associated with the points, for example their position in the reduced dimension space of the manifold, their associated gene transcript counts, etc. In particular, for the manifold of FIG. 7A, clustering assigned points to a given cluster based on a threshold similarity between the points in the manifold. For example, the points in the manifold of FIG. 7A that are included in group 8 are all likely associated with a mouse neuron, or other cells that are genetically similar to a mouse neuron. Similarly, the points in the manifold of FIG. 7A that are included in group 9 are all likely associated with a mouse myocyte, or other cells that are genetically similar to a mouse myocyte.

Figure 7B:
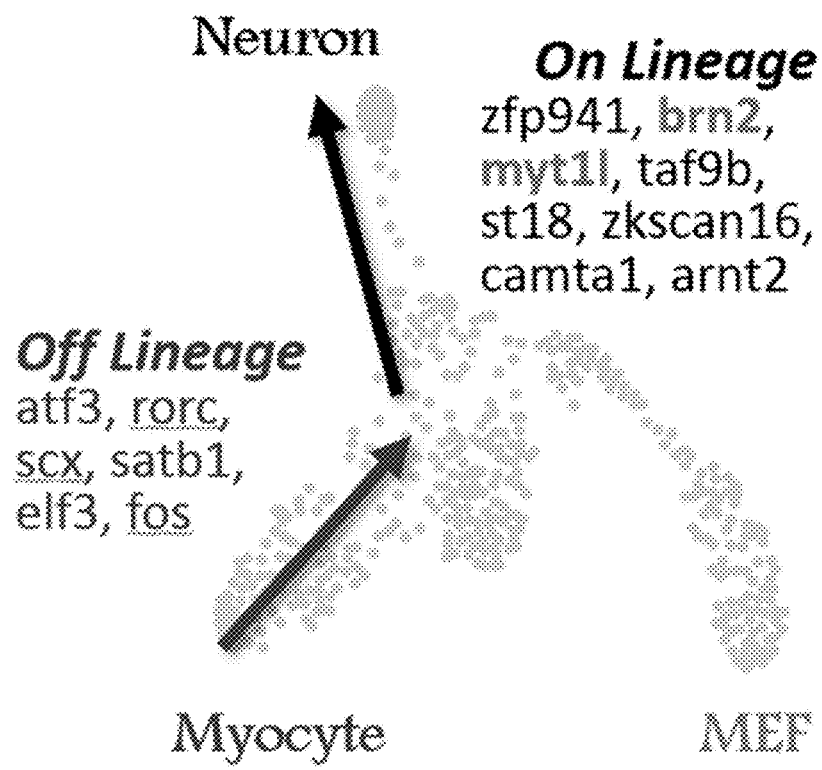
FIG. 7B depicts transcription factors that are both known and unknown in the literature to be associated with transition of a MEF to a mouse neuron, as opposed to a mouse myocyte, in accordance with an embodiment of the present disclosure.

As discussed above, in addition to enabling accurate identification of genes that are known in the literature to induce cell state transition, the methods of Section II and III also allow identification of factors (e.g., genes and perturbations) that impact cell state transition that are not known in the literature. FIG. 7B depicts transcription factors that are both known and unknown in the literature to be associated with transition of a MEF to a mouse neuron, as opposed to a mouse myocyte, in accordance with an embodiment. In particular, FIG. 7B depicts transcription factors that, when under-expressed in mouse "progenitor" cells, are associated with inhibiting transition of the mouse "progenitor" cells into mouse myocytes, and transcription factors that, when over-expressed in mouse "progenitor" cells, are associated with the transition of the mouse "progenitor" cells into mouse neurons. By under-expressing transcription factors that are associated with inhibiting transition of mouse "progenitor" cells into mouse myocytes in a mouse "progenitor" cell, and by over-expressing transcription factors that are associated with induction of transition of mouse "progenitor" cells into mouse neurons in the mouse "progenitor" cell, the mouse "progenitor" cell can be induced to transition into a mouse neuron, as opposed to a mouse myocyte.

To identify transcription factors that are associated with transition of a first cell state to an alternate, specific cell state, or from a first cell state to any other cell state, the clusters can be used. Specifically, gene transcript counts associated with the points in a cluster associated with the first cell state are identified and compared to the gene transcript counts associated with the points in another cluster associated with the alternate, specific cell state, or with any cell state other than the first cell state. This comparison of gene transcript counts between clusters can be performed using any differential expression test such as a difference of means test, a Wilcoxon Rank Sum Test, a t-test, logistic regression, and a generalized linear model.

As an example, to identify transcription factors that are associated with a transition from a MEF to a mouse neuron, the clusters discussed with respect to FIG. 7A were used. First, to identify the transcription factors that are associated with the transition of mouse "progenitor" cells into mouse neurons when over-expressed in the mouse "progenitor" cells, the gene transcript counts associated with the points included in the cluster of FIG. 7A that is associated with mouse neurons (e.g., cluster 8 of FIG. 7A) were identified and compared to the gene transcript counts associated with the points included in alternative clusters of FIG. 7A that are not associated with mouse neurons. In the embodiment of FIG. 7B, this comparison was performed using the Wilcoxon Rank Sum Test. However, in alternative embodiments, the comparison can be performed using any other method of statistical analysis. Based on this comparison, the genes that were over-expressed in cells associated with the points in the cluster of FIG. 7A that is associated with mouse neurons, were predicted to be associated with the transition of mouse "progenitor" cells into mouse neurons. The transcription factors that arise from transcription and translation of these genes were identified as the transcription factors in FIG. 7B that are associated with the transition of mouse "progenitor" cells into mouse neurons when over-expressed in the mouse "progenitor" cells.

Similarly, to identify the transcription factors that are associated with inhibiting transition of mouse "progenitor" cells into mouse myocytes when under-expressed in the mouse "progenitor" cells, the gene transcript counts associated with the points included in the cluster of FIG. 7A that is associated with mouse myocytes (e.g., cluster 9 of FIG. 7A) were identified and compared to the gene transcript counts associated with the points included in alternative clusters of FIG. 7A that are not associated with mouse myocytes. As noted above, in the embodiment of FIG. 7B, this comparison was performed using the Wilcoxon Rank Sum Test. However, in alternative embodiments, the comparison can be performed using any other method of statistical analysis. Based on this comparison, the genes that were under-expressed in cells associated with the points in the cluster of FIG. 7A that is associated with mouse myocytes, were predicted to be associated with inhibiting transition of mouse "progenitor" cells into mouse myocytes. The transcription factors that arise from transcription and translation of these genes were identified as the transcription factors in FIG. 7B that are associated with inhibiting transition of mouse "progenitor" cells into mouse myocytes when under-expressed in the mouse "progenitor" cells.

As seen in FIG. 7B, the transcription factors that are associated with the transition of mouse "progenitor" cells into mouse neurons when over-expressed in the mouse "progenitor" cells include Zfp941, Brn2, Mytl1, Taf5B, St18, Zkscan16, Camta1, and Arnt2. The transcription factors that are associated with inhibiting transition of mouse "progenitor" cells into mouse myocytes when under-expressed in the mouse "progenitor" cells include Atf3, Rorc, Scx, Satb1, Elf3, and Fos. As discussed in detail above with regard to Example 1, the Brn2 and Mytl1 transcription factors are known in the literature to be associated with induction of transition of a mouse "progenitor" cell into a mouse neuron. However, the remaining transcription factors depicted in FIG. 7B are not known in the literature to be associated with transition of a MEF to a mouse neuron, as opposed to a mouse myocyte. Therefore, by using the methods of Section II and Section III above, genes and/or transcription factors that are both known and not known in the literature to induce a cell to follow a specific trajectory of transition can be identified. These identified transcription factors can be then be used to control cell state transition, and thus cell fate.

IV.E. Example 3: Perturbation-Induced Transition

As discussed in Sections III.D and III.E, in addition to enabling identification of genes and transcription factors that impact cell state transition, the methods of Sections II and III also enable identification of perturbations, such as small molecules, that impact cell state transition. First, to identify perturbations that induce a cell to follow a particular trajectory of transition, the possible trajectories of transition are identified.

Figure 8A:
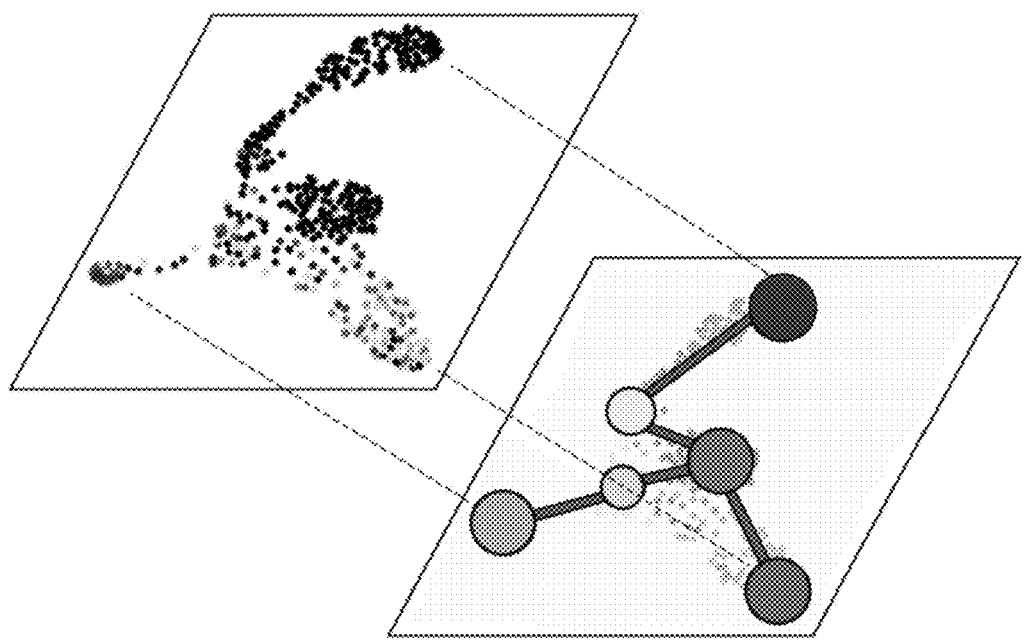
FIG. 8A depicts a map of transition trajectories for the MEF cells discussed with regard to FIG. 4A, in accordance with an embodiment of the present disclosure.

FIG. 8A depicts a map of transition trajectories for the MEF cells discussed with regard to FIG. 4A, in accordance with an embodiment. To construct this map of transition trajectories, the manifold of FIG. 4B was used. Specifically, points in the manifold that are associated with similar gene transcript counts were grouped into states (represented in FIG. 8A as circles). Points with variable gene transcript counts that are located between states were used to identify transition paths (represented in FIG. 8A as lines) between the states. The map of transition trajectories depicted in FIG. 8A can be used to identify perturbations that influence the transition trajectory of a cell by changing gene expression in the cell, and thereby causing the cell to progress from one state to another state in the map of transition trajectories. In some embodiments, to generate the map of transition trajectories depicted in FIG. 8A, cell typing via a set of canonical marker genes can be used. In such embodiments, cells that are identified as the same cell type are predicted to be cells along the same transition trajectory in the map of transition trajectories. In alternative embodiments, to generate the map of transition trajectories depicted in FIG. 8A, branches of the manifold of FIG. 4B are identified and predicted to define different transition trajectories in the map of transition trajectories.

Figure 8B:
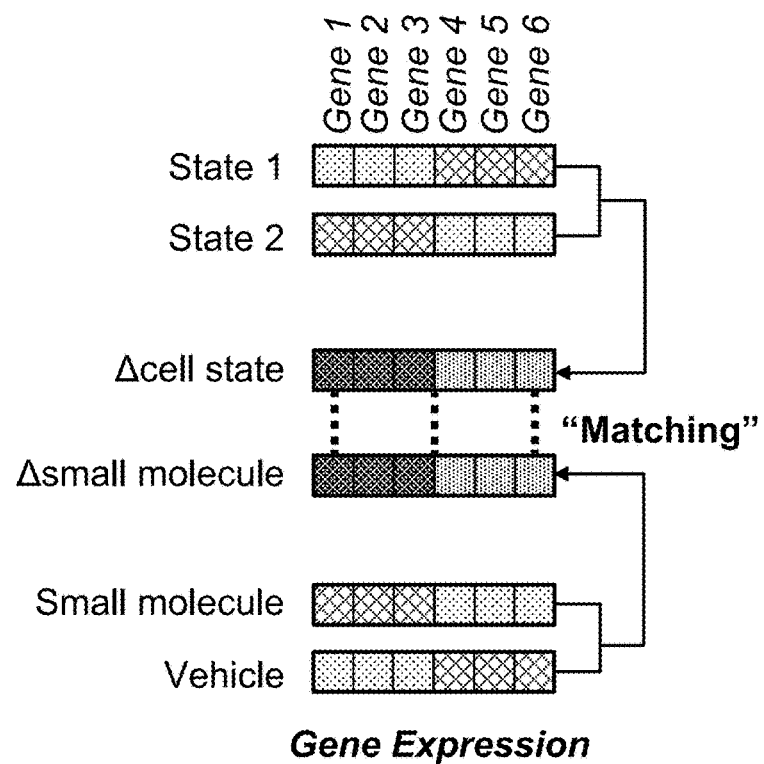
FIG. 8B depicts a method for identifying perturbations that influence the transition trajectory of a cell by changing gene expression in the cell such that the cell transitions from a first state to a second state in the map of transition trajectories of FIG. 8A, in accordance with an embodiment of the present disclosure.

FIG. 8B depicts an example of the method described in Section III.D. for identifying perturbations that influence the transition trajectory of a cell by changing gene expression in the cell such that the cell transitions from a first state to a second state in the map of transition trajectories of FIG. 8A, in accordance with an embodiment. Specifically, to identify a perturbation that, when exposed to a cell, causes the cell to change gene expression such that the cell transitions from a first state to a second state, the method of FIG. 8B compares a change in gene expression in a cell after the cell transitions from the first state to the second state, to a change in gene expression in a vehicle cell after the exposure of the vehicle cell to a perturbation. If the change in gene expression after the cell transitions from the first state to the second state matches (e.g., is equivalent or similar to) the change in gene expression in the vehicle cell after the exposure of the vehicle cell to a perturbation, then the perturbation can be predicted to induce transition of a cell exposed to the perturbation from the first state to the second state, by changing gene expression in the cell. In this way, a perturbation can be predicted to be associated with a particular trajectory of cell state transition.

Turning specifically to the example depicted in FIG. 8B, FIG. 8B depicts levels of gene expression for a cell in state 1, a cell in state 2, a vehicle cell, and the vehicle cell exposed to a small molecule perturbation, for six different genes, genes 1-6. The level of gene expression for a given gene is depicted by shading. Polka-dot shading indicates non-detectable gene expression, while cross-hatch shading indicates detectable gene expression. In other words, in the embodiment of FIG. 8B, gene expression is measured on a binary basis-detectable gene expression or non-detectable gene expression. However, in alternative embodiments, level of gene expression is not measured on a binary basis, but on a more quantitative basis.

Turning to examine the level of gene expression for each gene in each cell, for the cell in state 1, expression of genes 1-3 was non-detectable, but expression of genes 4-6 was detectable. Contrastingly, for the cell in state 2, expression of genes 4-6 was non-detectable, but expression of genes 1-3 was detectable. For the vehicle cell, expression of genes 1-3 was non-detectable, but expression of genes 4-6 was detectable. Contrastingly, for the vehicle cell exposed to the perturbation, expression of genes 4-6 was non-detectable, but expression of genes 1-3 was detectable.

Next, for each gene, the level of expression of the gene in the cell in state 1 was compared the level of expression of the gene in the cell in state 2, to determine a change in level of expression of the gene following transition of the cell from state 1 to state 2. As indicated by the darkened cross-hatch shading associated with genes 1-3, expression of genes 1-3 increased following transition of the cell from state 1 to state 2. On the other hand, as indicated by the darkened polka-dot shading associated with genes 4-6, expression of genes 4-6 decreased following transition of the cell from state 1 to state 2.

Similarly, for each gene, the level of expression of the gene in the vehicle cell was compared to the level of expression of the gene in the vehicle cell exposed to the perturbation, to determine a change in level of expression of the gene following exposure of the vehicle cell to the perturbation. As indicated by the darkened cross-hatch shading associated with genes 1-3, expression of genes 1-3 increased following exposure of the vehicle cell to the perturbation. On the other hand, as indicated by the darkened polka-dot shading associated with genes 4-6, expression of genes 4-6 decreased following exposure of the vehicle cell to the perturbation.

Finally, the change in gene expression in the cell following the transition of the cell from state 1 to state 2 was compared to the change in gene expression in the vehicle cell following exposure of the vehicle cell to the perturbation. To compare changes of gene expression in the transitioned cell to changes of gene expression in the vehicle cell, any differential expression test can be used. For example, any one of a difference of means test, a Wilcoxon Rank Sum Test, a t-test, logistic regression, and a generalized linear model comparison algorithm can be used.

As shown in FIG. 8B, expression of genes 1-3 was increased both in the cell that transitioned from state 1 to state 2, and in the vehicle cell that was exposed to the perturbation. Additionally, expression of genes 4-6 was decreased in both in the cell that transitioned from state 1 to state 2, and in the vehicle cell that was exposed to the perturbation. Based on this similarity in change in gene expression in the cell that transitioned from state 1 to state 2 and in the vehicle cell that was exposed to the perturbation, it can be predicted that exposure of a cell in state 1 to the perturbation can induce transition of the cell in state 1, to state 2, by changing gene expression in the cell. Therefore, the perturbation can be used to control transition of a cell from state 1 to state 2.

The method described above with regard to FIG. 8B relates to identification of perturbations that are associated with induction of transition of a cell from a generic state 1 to a generic state 2. Therefore, the method described above with regard to FIG. 8B can be used to identify perturbations that are associated with induction of transition of a cell from any state linked to any other state in the map of transition trajectories of FIG. 8A. However, rather than referring to generic states in the map of transition trajectories of FIG. 8A, FIG. 9 identifies specific states in the map of transition trajectories of FIG. 8A, and then identifies specific perturbations that are associated with induction or inhibition of transition of a cell from a one identified state to another identified state in FIG. 9, such that the cells become mouse neurons, as opposed to mouse myocytes. Specifically, FIG. 9 identifies an MEF state, a mouse "progenitor" cell state, a mouse myocyte state, and a mouse neuron state, and then identifies specific perturbations that are associated with induction or inhibition of a cell from a one of these state to another, such that the cells become mouse neurons, as opposed to mouse myocytes.

Figure 9:
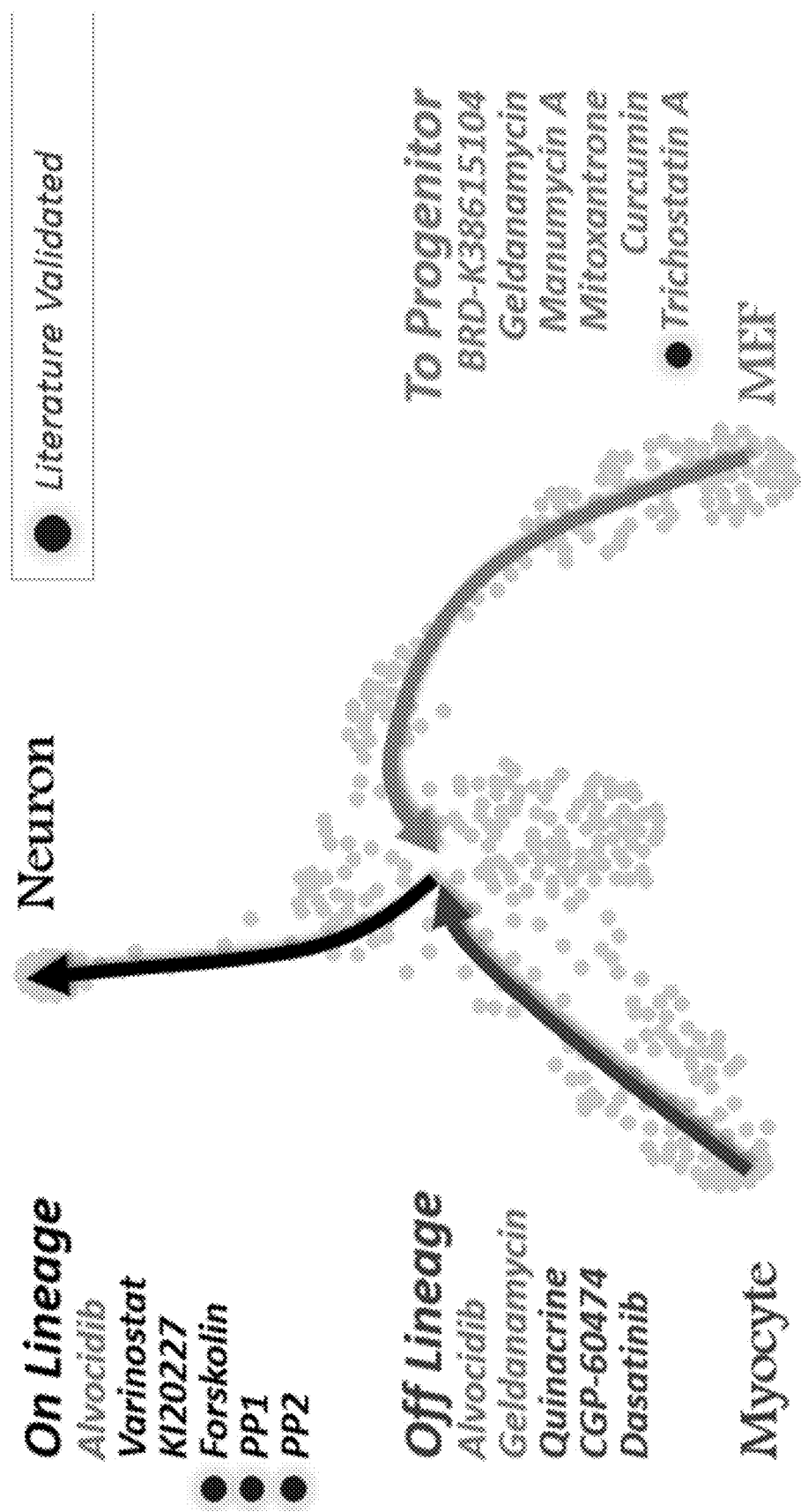
FIG. 9 depicts small molecule perturbations that are associated with transition of a MEF to a mouse neuron, as opposed to a mouse myocyte, in accordance with an embodiment of the present disclosure.

FIG. 9 depicts small molecule perturbations that are associated with transition of a MEF to a mouse neuron, as opposed to a mouse myocyte, in accordance with an embodiment. In particular, FIG. 9 depicts a set of small molecule perturbations that, when exposed to MEFs, are associated with the transition of the MEFs into mouse "progenitor" cells, a set of small molecule perturbations that, when exposed to mouse "progenitor" cells, are associated with inhibiting transition of the mouse "progenitor" cells into mouse myocytes, and small molecule perturbations that, when exposed to mouse "progenitor" cells, are associated with the transition of the mouse "progenitor" cells into mouse neurons. By exposing a MEF to perturbations that are associated with induction of transition of MEFs into mouse neurons, exposing the MEF to perturbations that are associated with inhibiting transition of mouse "progenitor" cells into mouse myocytes, and exposing the MEF to perturbations that are associated with induction of transition of mouse "progenitor" cells into mouse neurons, the MEF can be induced to transition into a mouse neuron, as opposed to a mouse myocyte.

Each of the small molecule perturbations depicted in FIG. 9 was identified by implementing the method described above with regard to FIG. 8B. For example, to identify the small molecule perturbation BRD-K38615104 as being associated with transition of a MEF into a mouse "progenitor" cell, it was determined using the method of FIG. 8B, that the change in gene expression in a MEF following transition of the MEF into a mouse "progenitor" cell matches (e.g., is equivalent or similar to) the change in gene expression in a vehicle cell after the exposure of the vehicle cell to BRD-K38615104. And therefore, BRD-K38615104 was predicted to induce transition of a MEF into a mouse "progenitor" cell by changing gene expression in the MEF. Similarly, to identify the small molecule perturbation Dasatinib, as being associated with inhibition of transition of a mouse "progenitor" cell into a mouse myocyte, it was determined using the method of FIG. 8B, that the change in gene expression in a mouse "progenitor" cell following transition of the mouse "progenitor" cell into a mouse myocyte is the inverse of the change in gene expression in a vehicle cell after the exposure of the vehicle cell to Dasatinib. And therefore, Dasatinib was predicted to inhibit transition of a mouse "progenitor" cell into a mouse myocyte.

As seen in FIG. 9, the small molecule perturbations that, when exposed to MEFs, are associated with the transition of the MEFs into mouse "progenitor" cells, include BRD-K38615104, Geldanamycin, Manumycin A, Mitoxantrone, Curcumin, and Trichostatin A. The small molecule perturbations that, when exposed to mouse "progenitor" cells, are associated with the transition of the mouse "progenitor" cells into mouse neurons, include Alvocidib, Varinostat, KI20227, Forskolin, PP1, and PP2. The small molecule perturbations that, when exposed to mouse "progenitor" cells, are associated with inhibition of transition of the mouse "progenitor" cells into mouse myocytes, include Alvocidib, Geldanamycin, Quinacrine, CGP-60474, and Dasatinib.

Two of the small molecule perturbations identified in FIG. 9, Alvocidib and Geldanamycin, are associated with induction of transition of a mouse cell to a mouse neuron by inducing and/or inhibiting transition of the mouse cell in two different states. Specifically, as shown in FIG. 9, Alvocidib is associated both with inducing transition of a mouse "progenitor" cell to a mouse neuron, and with inhibiting transition of a mouse "progenitor" cell to a mouse myocyte. Similarly, Geldanamycin is associated both with inducing transition of a MEF to a mouse "progenitor" cell, and with inhibiting transition of a mouse "progenitor" cell to a mouse myocyte. Therefore, by exposing a MEF to both Alvocidib and Geldanamycin, the MEF can be predicted to transition into a mouse neuron.

Some of the small molecule perturbations identified in FIG. 9 are known in the literature to be associated with the indicated trajectory of transition. Specifically, Forskolin, PP1, and PP2 are known in the literature to be associated with induction of transition of a mouse "progenitor" cell into a mouse neuron. Similarly, Trichostatin A is known in the literature to be associated with induction of transition of a MEF into a mouse "progenitor" cell. This consistency of predictions made by the method of FIG. 8B and information known in the literature demonstrates the ability of the method of FIG. 8B to accurately identify perturbations that influence cell state transition.

In addition to accurately identifying perturbations that are known in the literature to influence cell state transition, the method of FIG. 8B is also capable of identifying perturbations that are not known in the literature to influence cell state transition. Specifically, the remaining small molecule perturbations depicted in FIG. 9 are not known in the literature to be associated with transition of a MEF to a mouse neuron, as opposed to a mouse myocyte. Thus, by using the method described above with regard to FIG. 8B, perturbations that are both known and unknown in the literature to induce a cell to follow a specific trajectory of transition can be identified. These identified perturbations can then be used to control cell state transition, and thus cell fate.

V. Example 4

Figure 10A:
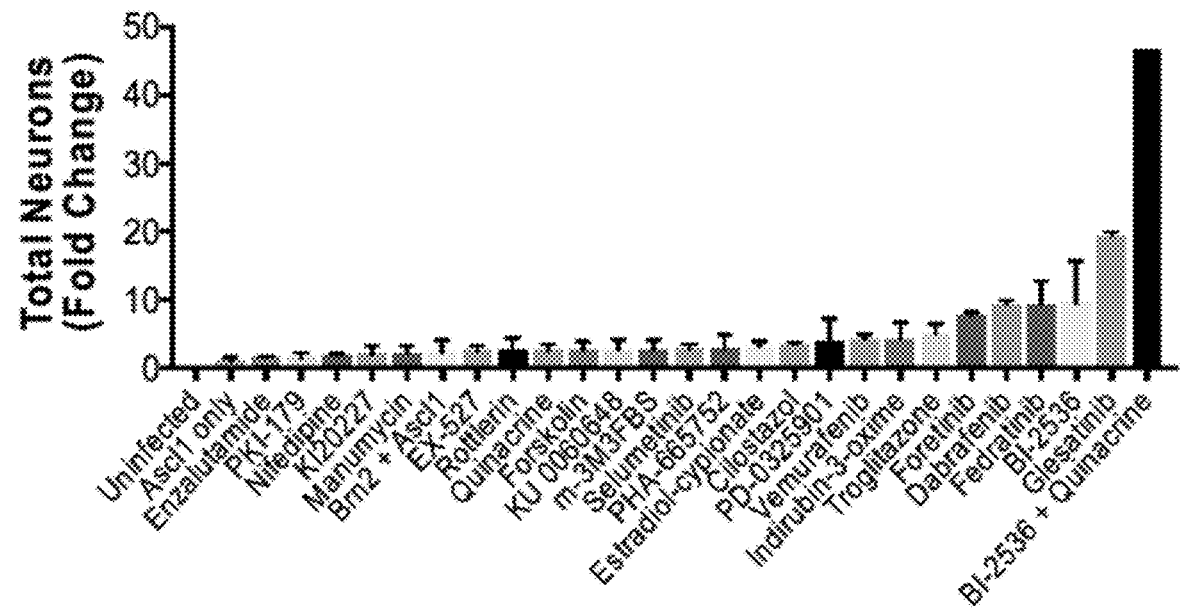
FIG. 10A provides a bar graph showing the total number of neuron for each treatment condition, wherein the total number of neurons was counted manually based on positive Tuj1/Map2 signal and neuronal morphology, and wherein for each experiment, the data of each treatment condition was normalized by the number of neurons in the DMSO treated wells, in accordance with an embodiment of the present disclosure.
Figure 10B:
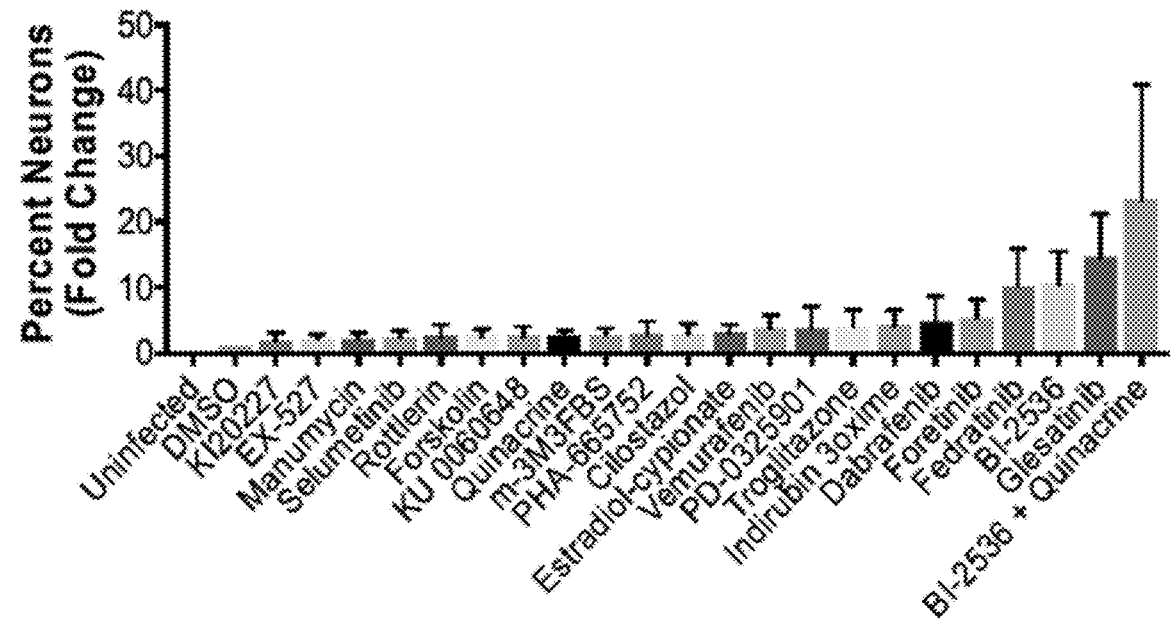
FIG. 10B provides a bar graph showing the percent neurons for each treatment condition, in accordance with an embodiment of the present disclosure.

The experiments of this example demonstrated a method for promoting neurons and/or progenitor cells. In the experiments described herein, a starting population of fibroblasts (i.e., primary mouse fibroblasts) were exposed to a composition including an Ascl1 overexpression lentiviru. After 48 hours, a compound (e.g., Forskolin, Glesatinib, PD-0325901), or a vehicle (i.e., DMSO or ethanol) was added to the composition. The total number of neurons were counted manually based on a positive Tuj1/Map2 signal and neuronal morphology. For each experiment, the total number of neurons for each treatment condition were normalized by the number of neurons in the DMSO treated wells relative to that experiment. As shown in FIG. 10A and FIG. 10B, the presence of neurons, which developed from the starting population of fibroblasts, were detected in these experiments. The fold change in both the total number of neurons and the percentage of neurons increased, decreased, or remained the same depending on the compound added to the composition. These experiments demonstrated that the methods of the present invention are useful in promoting neurons and/or progenitor cells from a starting population of cells including fibroblasts.

Cell Culture and Compound Treatment

Primary mouse embryonic fibroblasts (MEFs) at passage 2 were plated on 24 well plates at 20,000-45,000/well (depending on lot) in MEF culture media including 10% FBS in DMEM, 1× Glutamax, 1× MEM Non-essential amino acids, 1 mM Sodium pyruvate, 0.05 U/ml pen/strep, and 55 µM beta-Mercaptoethanol. After 24 hours in culture, MEFs were infected with Ascl1 overexpressing lentivirus in MEF culture media containing 8 µg/ml polybrene via spinfection (plates spun at 2000 rpm at 32° C. for 90 minutes). See below for lentivirus generation. After 48 hours, media was changed to Neuronal media including DMEM/F12, 1% N2, 2% B27 1:50, 1× Glutamax, 25 µg/ml Insulin, 0.05 U/ml pen/strep containing a compound or vehicle (DMSO or ethanol). Compounds and their concentration were selected from the following: BI-2536 (200 nM), Cilostazol (1000 nM), Dabrafenib (2500 nM), Estradiol-cypionate (2000 nM), EX-527 (5000 nM), Fedratinib (1000 nM), Foretinib (200 nM), Forskolin (5000 nM), Glesatinib (2500 nM), Indirubin 3oxime (2000 nM), KI20227 (250 nM), KU 0060648 (200 nM), m-3M3FBS (1000 nM), Manumycin (800 nM), PD-0325901 (5000 nM), PHA-665752 (1000 nM), Quinacrine (200 nM), Rottlerin (1000 nM), Selumetinib (100 nM), Troglitazone (5000 nM), and Vemurafenib (5000 nM). Half-media changes were performed every 2-3 days with supplemented compounds.

Immunofluorescence Staining

At day 12 post Ascl1 infection, cells were fixed with 4% paraformaldehyde, permeabilized (0.2% Triton X100) and blocked in 5% serum (donkey, calf, goat serum mix), and stained with rabbit anti-Tuj1 (1:1000) and mouse anti-Map2 (1:500) antibodies overnight at 4° C., or 2 hours at room temperature, followed by secondary antibody and DAPI staining.

Imaging and Analysis

Imaging was carried out on Molecular Devices ImageXpress Micro; 36 images per well were taken on 10× objective. Total number of neurons was counted manually based on positive Tuj1/Map2 signal and neuronal morphology. For each experiment, total number of neurons for each treatment condition was normalized by the number of neurons in the DMSO treated wells for that experiment.

Lentivirus Generation

Lentivirus was packaged by transfecting 293T cells via Mirus TransIT Lenti Tranfection Reagent (Mirus, MIR 6603) with Packaging plasmids (SystemsBio, LV51OA-1) or similar, and Ascl1 overexpression plasmid (Ascl1 cDNA cloned into Origene lentiviral expression vector cat #PS100064), and concentrated in BeckmanCoulter ultracentrifuge for 1.5 hours at 16,500 RPM. Only experiments with lentiviral infection of 90% of more cells, as judged by rabbit anti-Ascl1 (1:200; Abcam, ab74065-100UG) immunofluorescence staining at 48 hours were pursued.

V. Example 5

Embodiment 1. A method for predicting whether a perturbation will affect a cellular transition, the method comprising: at a computer system comprising a memory and one or more processors: accessing, in electronic form, a single-cell transition signature representing a measure of differential cellular-component expression between a first cell state and an altered cell state, wherein the altered cell state occurs through the cellular transition from the first cell state to the altered cell state, and wherein the single-cell transition signature comprises an identification of a plurality of cellular-components and, for each respective cellular-component in the plurality of cellular-components, a corresponding first significance score that quantifies an association between a change in expression of the respective cellular-component and a change in cell state between the first cell state and the altered cell state; accessing, in electronic form, a perturbation signature representing a measure of differential cellular-component expression between a plurality of unperturbed cells and a plurality of perturbed cells exposed to the perturbation, wherein the perturbation signature comprises an identification of all or a portion of the plurality of cellular-components and, for each respective cellular-component in the all or the portion of the plurality of cellular-components, a corresponding second significance score that quantifies an association between (i) a change in expression of the respective cellular-component between the plurality of unperturbed cells and the plurality of perturbed cells and (ii) a change in cell state between the plurality of unperturbed cells and the plurality of perturbed cells; and comparing the single-cell transition signature and the perturbation signature thereby determining whether the perturbation will affect the cellular transition.

Embodiment 2. The method of embodiment 1, wherein accessing the single-cell transition signature comprises: determining the single-cell transition signature based on (i) a first plurality of first single-cell cellular-component expression datasets, and (ii) a second plurality of second single-cell cellular-component expression datasets, wherein: each respective first single-cell cellular-component expression dataset in the first plurality of first single-cell cellular-component expression datasets is obtained from a corresponding single cell of a first plurality of cells in the first cell state, and each respective second single-cell cellular-component expression dataset in the second plurality of second single-cell cellularity component expression datasets is obtained from a corresponding single cell of a second plurality of cells in the altered cell state.

Embodiment 3. The method of embodiment 2, wherein: each respective dataset of the first plurality of single-cell cellular-component expression datasets comprises a corresponding cellular-component vector, in a first plurality of cellular-component vectors, each respective dataset of the second plurality of single-cell cellular-component expression datasets comprises a corresponding cellular-component vector, in a second plurality of cellular-component vectors, each respective cellular-component vector in the first and second plurality of cellular-component vectors comprises a plurality of elements, each respective element in the respective cellular-component vector associated with a corresponding cellular-component in the plurality of cellular-components and including a corresponding value that represents a quantity of the corresponding cellular-component for the corresponding single cell that is represented by the respective dataset of the first and second pluralities of single-cell cellular-component expression datasets.

Embodiment 4. The method of embodiment 3, further comprising: performing dimensionality reduction on the first and/or the second plurality of single-cell cellular-component expression datasets to generate a plurality of dimension reduction components; applying, for each respective cellular-component vector in the first and second plurality of cellular-component vectors, the plurality of dimension reduction components to the respective cellular-component vector to form a corresponding dimension reduction vector that includes a dimension reduction component value for each respective dimension reduction component in the plurality of dimension reduction components, thereby forming a corresponding first and second plurality of dimension reduction vectors; and performing clustering to generate a set of clusters $C_j$, each cluster comprising a plurality of points corresponding to a subset of the first and second plurality of dimension reduction vectors; identifying the first plurality of cells from a first cluster of the set of clusters $C_j$; and identifying the second plurality of cells from a second cluster of the set of clusters $C_j$, the method optionally further comprising performing manifold learning with the corresponding first and second plurality of dimension reduction vectors to identify a relative cell state of each cell with respect to each other cell in the first and second plurality of cells.

Embodiment 5. The method of any one of embodiments 1-4, wherein the plurality of unperturbed cells are control cells that have not been exposed to the perturbation, or wherein the unperturbed cells are an average taken over unrelated perturbed cells that have been exposed to the perturbation.

Embodiment 6. The method of any one of embodiments 1-5, the method further comprising: pruning the single-cell transition signature and the perturbation signature to limit the plurality of cellular-components to transcription factors, optionally measured at the RNA level.

Embodiment 7. The method of embodiment 2, wherein the determining the single-cell transition signature comprises: determining a difference in cellular-component quantities across the plurality of cellular-components between (i) the first plurality of first single-cell cellular-component expression datasets and the second plurality of second single-cell cellular-component expression datasets using one of a difference of means test, a Wilcoxon rank-sum test, a t-test, a logistic regression, and a generalized linear model.

Embodiment 8. The method of embodiment 1, wherein the measure of differential cellular-component expression quantifies a difference in cellular-component quantities between (i) a third plurality of third single-cell cellular-component expression datasets and (ii) a fourth plurality of fourth single-cell cellular-component expression datasets using one of a Wilcoxon rank-sum test, a t-test, a logistic regression, and a generalized linear model, wherein: each respective third single-cell cellular-component expression dataset in the third plurality of third single-cell cellular-component expression datasets is obtained from a corresponding single cell of in the plurality of unperturbed cells, and each respective fourth single-cell cellular-component expression dataset in the fourth plurality of fourth single-cell cellularity component expression datasets is obtained from a corresponding single cell of a fourth plurality of cells in the plurality of perturbed cells exposed to the perturbation.

Embodiment 9. The method of any one of embodiments 1-8, further comprising: filtering the single-cell transition signature and the perturbation signature to reduce a number of cellular-components included in the single-cell transition signature and the perturbation signature, optionally wherein the filtering the single-cell transition signature and the perturbation signature comprises reducing the number of cellular-components included in the single-cell transition signature and the perturbation signature according to a threshold p-value or according to a threshold number of cellular-components.

Embodiment 10. The method of any one of embodiments 1-9, wherein determining the corresponding second significance score for a respective cellular-component comprises: replacing the significance score for the respective cellular-component with a corresponding matching score for the respective cellular-component, for each respective cellular-component in the plurality of cellular-components; combining the matching scores for the plurality of cellular-components to generate a matching score for the perturbation; and determining whether the perturbation is associated with the transition of cells between the first cell state and the altered cell state based on the matching score for the respective perturbation, optionally wherein the corresponding matching score comprise discrete or continuous score.

Embodiment 11. The method of embodiment 10, wherein replacing the significance score comprises: replacing the significance score with a first score if the cellular-component quantity from the single-cell transition signature for the respective cellular-component and the cellular-component quantity from the perturbation signature for the respective cellular-component are both up-regulated; replacing the significance score with a second score if the cellular-component quantity from the single-cell transition signature for the respective cellular-component is up-regulated and the cellular-component quantity from the perturbation signature for the respective cellular-component is down-regulated; and replacing the significance score with a third score if the cellular-component quantity from the perturbation signature for the respective cellular-component is not significantly up-regulated or down-regulated.

Embodiment 12. The method of embodiment 10, wherein replacing the significance score comprises: replacing the significance score with a first score if the cellular-component quantity from the single-cell transition signature for the respective cellular-component and the cellular-component quantity from the perturbation signature for the cellular-component are both down-regulated; replacing the significance score with a second score if the cellular-component quantity from the single-cell transition signature for the respective cellular-component is down-regulated and the cellular-component quantity from the perturbation signature for the cellular-component is up-regulated; and replacing the significance score with a third score if the cellular-component quantity from the perturbation signature for the cellular-component is not significantly up-regulated or down-regulated.

Embodiment 13. The method of any one of embodiments 1-12, wherein the plurality of cellular-components comprise a plurality of genes, optionally measured at the RNA level.

Embodiment 14. The method of embodiment 2, wherein each single-cell cellular-component expression dataset in the first plurality of first single-cell cellular-component expression datasets and the second plurality of second single-cell cellular-component expression datasets is generated using a method selected from the group consisting of: single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combinations thereof, as well as summaries of the same, including combinations, such as linear combinations, representing activated pathways in the single-cell cellular-component expression datasets.

Embodiment 15. The method of any one of embodiments 1-14, the method further comprising: identifying the perturbation as one that promotes the altered cell state based on the comparing, or identifying the perturbation as one that inhibits the altered cell state based on the comparing.

Embodiment 16. The method of any one of embodiments 1-15, wherein the cell transition signature and the perturbation signature are generated using different types of cellular-components.

Embodiment 17. The method of any one of embodiments 1-16, wherein the cell transition signature and the perturbation signature are generated using the same types of cellular-components.

Embodiment 18. The method of any one of embodiments 1-17, wherein the accessing, in electronic form, is performed for each respective signature in a plurality of perturbations, thereby obtaining a plurality of perturbation signatures the comparing compares the single-cell transition signature and the perturbation signature to each respective signature in a plurality of perturbation signatures, thereby determining a subset of the plurality of perturbations that are associated with the transition of cells between the first cell state and the altered cell state.

Embodiment 19. A computer system, comprising one or more processors and memory, the memory storing instructions for performing the method of any one of embodiments 1-18.

Embodiment 20. A non-transitory computer-readable medium storing one or more computer programs executable by a computer for predicting whether a perturbation will affect a cellular transition, the computer comprising one or more processors and a memory, the one or more computer programs collectively encoding computer executable instructions for performing the method of any one of embodiments 1-18.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIG. 1 or 2. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method comprising:
A) performing, using a database processing system comprising one or more processors and a memory, a first database access call to access a single-cell transition signature representing a measure of differential cellular-component amount between a normal cell state and a diseased cell state, wherein the diseased cell state occurs through a transition, free of a perturbation, from the normal cell state to the diseased cell state, and wherein the first database access call identifies a plurality of cellular-components comprising at least 1000 cellular-components and, for each respective cellular-component in the plurality of cellular-components, a corresponding first association between (a) a change in amount of the respective cellular-component in a first plurality of first cellular-datasets and a second plurality of second cellular-component datasets and (b) a change in state between the normal state and the diseased cell state, wherein:
each respective first cellular-component dataset in the first plurality of first cellular-component datasets comprises amount data for the plurality of cellular-components for a corresponding single cell of a first sample of cells in the normal state,
the first plurality of first cellular-component datasets includes a respective first cellular-component dataset for each single cell of the first sample of cells and the first sample of cells comprises at least 10,000 cells,
each respective second cellular-component dataset in the second plurality of second cellular-component datasets comprises amount data for the plurality of cellular-components for a corresponding single cell of a second sample of cells in the diseased cell state, and
the second plurality of second cellular-component datasets includes a respective second cellular-component dataset for each single cell of the second sample of cells and the second sample of cells comprises at least 10,000 cells;
B) performing, using the database processing system, a second database access call to access a perturbation signature representing a measure of differential cellular-component amount between (i) a third sample of cells exposed to a vehicle and (ii) a fourth sample of cells, wherein the fourth sample of cells are exposed to the perturbation and the vehicle, wherein the perturbation signature comprises an identification of all or a portion of the plurality of cellular-components and, for each respective cellular-component in the all or the portion of the plurality of cellular-components, a corresponding second association between a change of amount of the respective cellular-component between a third plurality of cellular-component datasets and a fourth plurality of cellular-component datasets, wherein the third sample of cells, prior to exposure to the vehicle, are in the same state as the fourth sample of cells, prior to the exposure of the vehicle and the perturbation, wherein
each respective cellular-component dataset in the third plurality of third cellular-component datasets comprises amount data for the plurality of cellular-components for a corresponding single cell in the third sample of cells,
the third plurality of third cellular-component datasets includes a respective third cellular-component dataset for each single cell of the third sample of cells and the third sample of cells comprises at least 10,000 cells,
each respective cellular-component dataset in the fourth plurality of fourth cellular-component datasets comprises amount data for the plurality of cellular-components for a corresponding single cell in the fourth sample of cells, and
the fourth plurality of fourth cellular-component datasets includes a respective fourth cellular-component dataset for each single cell of the fourth sample of cells and the fourth sample of cells comprises at least 10,000 cells;
C) determining that the perturbation affects the transition, using the database processing system, and using (i) first associations in the single-cell transition signature and (ii) corresponding second associations in the perturbation signature; and D) applying the perturbation to a subject that has a disease associated with the diseased state, thereby treating the subject.

2. The method of claim 1, wherein the perturbation is a small molecule.

3. The method of claim 1, wherein the perturbation is a protein.

4. The method of claim 1, wherein the perturbation is a nucleic acid.

5. The method of claim 1, wherein the plurality of cellular-components comprises 10,000 cellular-components.

6. The method of claim 1, wherein
the fourth sample of cells are in the diseased cell state prior to being exposed to the perburbation and the vehicle, and
the third sample of cells are in the normal state.

7. The method of claim 1, wherein the vehicle is dimethyl sulfoxide or ethanol.

8. The method of claim 1, wherein the determining C) makes use of a trained neural network model.

9. The method of claim 1, the method further comprising determining that the second sample of cells are in the diseased cell state by determining that second sample of cells have incurred a loss of a cell function.

10. The method of claim 1, the method further comprising determining that the second sample of cells are in the diseased cell state by determining that second sample of cells have incurred a gain of a cell function.

11. The method of claim 1, the method further comprising:
identifying a plurality of covariates of the perturbation, wherein the plurality of covariates includes (i) a dose of the perturbation or (ii) an identity of a cell line exposed to the perturbation, and wherein the determining C) determines at least two of the plurality of covariates of the perturbation affects the transition.

12. The method of claim 1, wherein the determining C) further uses a false cellular-component discovery rate for the perturbation to determine that the perturbation affects the transition.

13. The method of claim 1, wherein the plurality of cellular constituents consists of transcription factors.

14. The method of claim 1, the method further comprising filtering the single-cell transition signature or the perturbation signature by application of a p-value prior to the determining C).

15. The method of claim 1, wherein the plurality of cellular-components of the single-cell transition signature or the perturbation signature consists of between 10 and 25 cellular components.

* * * * *